US007335733B2

(12) United States Patent
Paesen et al.

(10) Patent No.: US 7,335,733 B2
(45) Date of Patent: Feb. 26, 2008

(54) **TISSUE CEMENT PROTEINS FROM *RHIPICEPHALUS APPENDICULATUS***

(75) Inventors: Guido Christian Paesen, Oxford (GB); Patricia Ann Nuttall, Cullham (GB)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 10/226,489

(22) Filed: Aug. 23, 2002

(65) Prior Publication Data

US 2003/0078390 A1    Apr. 24, 2003

Related U.S. Application Data

(63) Continuation of application No. 09/554,547, filed as application No. PCT/GB98/03397 on Nov. 12, 1998, now abandoned.

(30) Foreign Application Priority Data

Nov. 12, 1997 (GB) ................................. 9723945.3

(51) Int. Cl.
*C07K 14/435* (2006.01)
*A61K 39/00* (2006.01)
*C12N 1/16* (2006.01)
*C12N 15/74* (2006.01)

(52) U.S. Cl. .................... 530/350; 530/395; 424/184.1; 424/185.1; 424/191.1; 424/194.1; 435/69.1; 435/69.7; 435/254.3; 435/320.1; 435/485; 536/23.1; 536/23.4; 536/23.7

(58) Field of Classification Search ............... 536/23.1, 536/23.4; 435/320.1, 69.1; 424/192.1, 194.1, 424/184.1; 530/300, 350
See application file for complete search history.

(56) References Cited

OTHER PUBLICATIONS

Roitt et al, 1998, Immunology, p. 7.7, 7.8 4th ed, Mosby, London.*
Holmes (Exp. Opin.Invest. Drugs. 2001, 10(3):511-519.*
Herbert et al. (The Dictionary of Immunology.*
Greenspan et al., Nature Biotechnology 7:936-937 (1999).*
Bowie et al (Science, 190, 257:1306-1310).*
Brown et al., Experimental Parasitology, 62:40-50 (1986).
Crampton et al., "Expression sequenced tags and new genes from the cattle tick, Boophilus microplus" EMBL Sequence Dtabase, Sep. 11, 1997, Heidelberg, FRG, *Boophilus microplus* EST 198 putative nuclear antigen mRNA sequence; Accession No. U92768; & Exp. Appl. Acarol., vol. 22, No. 3, 1998, pp. 117-186.
Jaworski et al., Journal of Medical Entomology, 29:305-309 (1992).
Jaworski et al.,F. Dusbabek and V. Bukva (Eds.):Modern Acarology, Academia, Prague and SPB Academic Publishing bv, The Hague, 1:335-340 (1991).
Needham et al., Experimental & Applied Acarology, 7:21-32 (1989).
Wang et al., Parasitology, 109:517-523 (1994).

Mirendorf et al., Methods Enzymol., 152: 556-62, 1987.
Moorhouse et al., Parasitology, 56: 623-32, 1966.
Needham et al., Exp. And Applied Acarology, 7: 21-32, 1989.
Norval et al., Tick Vector Biology-Medical and Vet. Aspects, 1992.
Norval et al., The Epidemiology of Theileriosis in Africa, 1992.
O'Reilly et al., Baculovirus Expression Vectors: A Lab. Manual, 1994.
Sambrook et al., Molecular Cloning: A Lab. Manual, $2^{nd}$ ed., 1989.
Sanger et al., J Mol. Biol., 94: 441-48, 1975.
Schagger et al., Analytical Biochem., 166: 368-79, 1987.
Shapiro et al., Exp. & Applied Acarology, 7: 33-41, 1989.
Shapiro et al., J. Parasit, 72(3), 454-63, 1986.
Siegel, Int. Rev. of Conn. Tissue Res., 8: 73-118, 1979.
Sononshine, Biology of Ticks, vol. 1, 1991.
Sugumaran et al., Archives of Insect Biochem. and Phys., 19: 271-83, 1992.
Walker et al., Int. J. of Parasitology, 15(1): 81-100, 1985.
Wang et al., Parasitology, 109: 517-23, 1994.
Watson et al., Recombinant DNA($2^{nd}$. Ed.), 1994.
Anderson, J of Biochem and Biophys. Methods, 10: 203-9, 1984.
Arthur, Parasitology, 41: 66-81, 1951.
Brown et al., Experimental Parasitology, 62(1): 40-50, (1986).
Bugge et al., EMBO J., 11(4): 1409-18, 1992.
Crampton et al., EMBL Sequence Database, 22(3): 177-86, (1998)'1.
Creighton T., Protein Structure-A practical approach, IRL Press, 155-168.
Davies, The Arboviruses: Epidemiology and Ecology, vol. III: 191-203.
Goode et al., Biotechniques, 12(3): 374-75, 1992.
Ichinose et al., JBC, 265: 13411-14, 1990.
Janknecht et al., PNAS, 88: 8972-76, 1991.
Jaworski et al., Modern Acarology, 1: 335-40, 1991.
Jaworksi et al., J. Med. Entomol., 29(2): 305-9, 1992.
Kemp, Physiology of Ticks, p. 119-68, 1982.
Laemmli, Nature, 227, 680-685.
Lu et al., Analytical Biochem., 213: 318-22, 1993.
Matsudaira, JBC, 262(21): 10035-8, 1987.
Malencik et al., Anal. Biochem., 242: 202-13, 1996.

* cited by examiner

*Primary Examiner*—Jeffrey Siew
*Assistant Examiner*—Padma Baskar
(74) *Attorney, Agent, or Firm*—Judy Jarecki-Black; Frommer, Lawrence & Haug

(57) ABSTRACT

The present invention relates to tissue cement proteins produced by certain species of blood-feeding ectoparasites. These proteins and compositions comprising these proteins are particularly useful for the temporary or permanent bonding of animal tissues to each other or to other biomaterials. The present invention also relates to the use of tissue cement proteins in the production of vaccines that protect animals against the bite of blood-sucking ectoparasites and the transmission of viruses, bacteria and other pathogens by such ectoparasites.

14 Claims, 19 Drawing Sheets

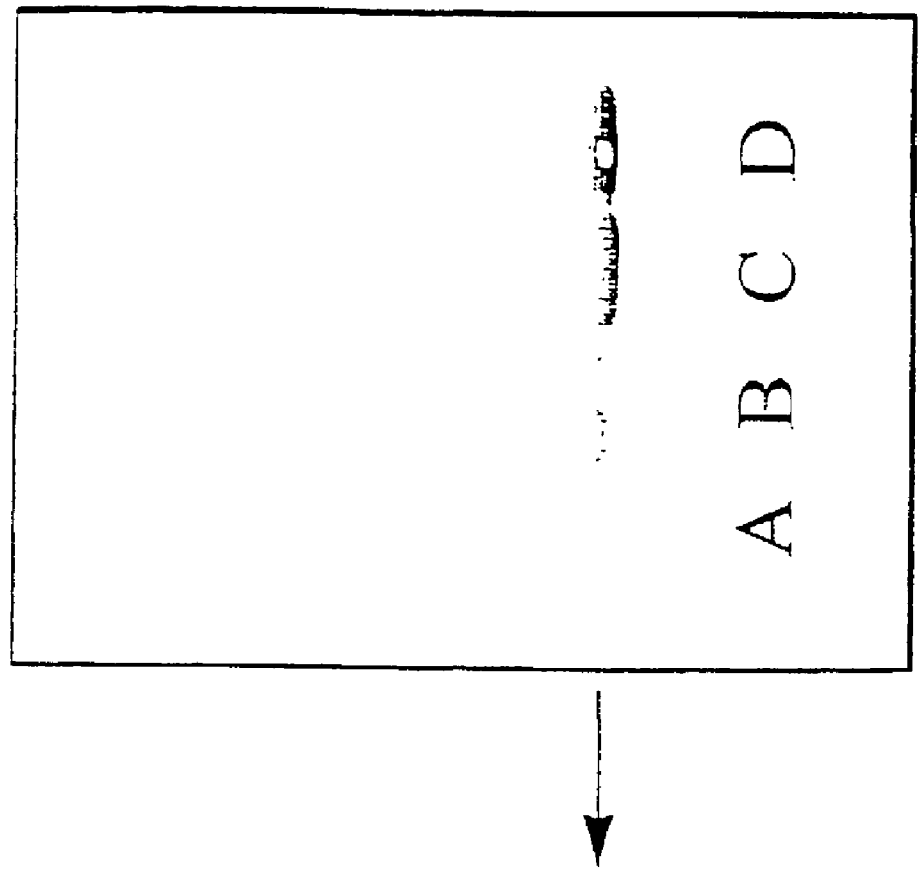
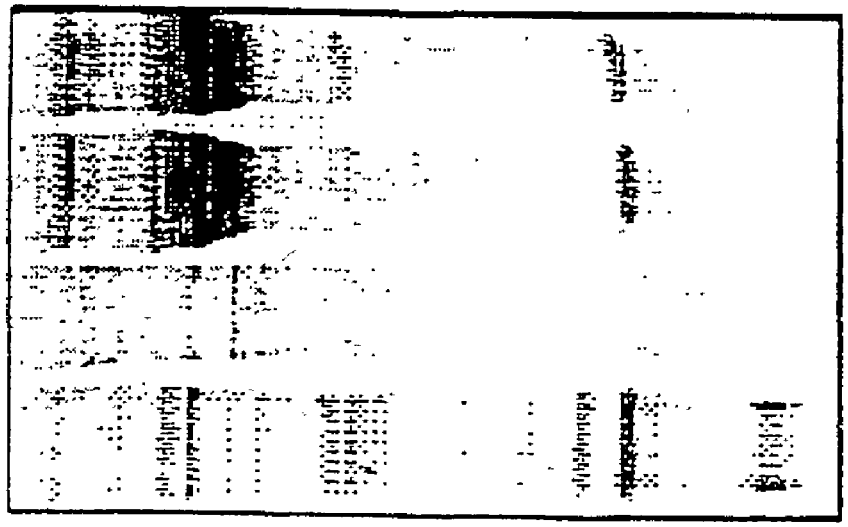
FIG. 1B
FIG. 1A

FIG. 2

```
1    AAACCAAGGCAGGACACAGCCAGCCATGAAGGCCTTCGTTGCAGTCGCCCTTTTGTCTGCA    60
                         M  K  A  F  V  A  V  A  L  L  S  A

61   GTTTCCGTGGCACATGCTGCCCTCAAGACTGACGTAGCCAGTGGACCTGCCGGTTCTGGT   120
     V  S  V  A  H  A  A  L  K  T  D  V  A  S  G  P  A  G  S  G

121  GCACTAAGTCTAGGAGTTGGAGGCTTCCCGTCCGGTGCTTCGCTTGGCAGCCTTAGTGGC   180
     A  L  S  L  G  V  G  G  F  P  S  G  A  S  L  G  S  L  S  G

181  GTAACCCTCTCTGGTGCTGGTCTCTTCCGTGTCTGGCCGCCCCTGGATCCCCTGGAGCT   240
     V  T  L  S  G  A  G  S  S  V  S  G  R  P  G  S  P  G  S  A

241  GGTCCTAGCTCTCTGGACCCCGCAGTGTCG   267
     G  P  S  S  G  P  A  V  S
```

FIG. 3

```
  1  CGGACGCACACTCCTGCAGGAAGGTCATCTAGTTCCGCCAACATGAAGCTGCTCTGTGCA   60
                                         M  K  L  L  C  A

61  CTAGCCCTCGTTGCCCTTGGACTTCCATTCGGCAGCGCTTACCTTGGTGGCTTCGGCGGC  120
      L  A  L  V  A  L  G  L  P  F  G  S  A  Y  L  G  G  F  G  G

121  CTCGGTGGTTGGGGGGGTCTCGGTGCCATCTTTGGCCCCAGGAGCTTATCCCGGTTTC    180
      L  G  G  W  G  G  G  L  G  A  I  F  G  P  G  A  Y  P  G  F

181  TATGGCCTTAACAGCGTGCACCTCTTGGGCGGCAGTTCCACCATCTCTTCGGGCGATTC   240
      Y  G  L  N  S  V  H  L  L  G  G  R  F  H  H  L  F  G  R  F

241  CCGCCACCACCCGGTATTGGAGCTGCTGAAGCGCAGGGGAACCTAAGCCCATACCCCTCTT 300
      P  P  P  P  G  I  G  A  A  E  A  Q  G  N  L  S  P  Y  P  L

301  GACATCAACACCGTCCAAGACCCGAACTGGCCACCCCATGGTACGCGTTGTCTACGGCGG  360
      D  I  N  T  V  Q  D  P  N  W  P  P  H  G  T  R  C  L  R  R

361  AGTCTTGCGGGAGCCTCTGACCCTGACCAGTCCCAATTCCACAGGATGTGCCTGTCCC    420
      S  L  A  G  A  P  L  T  L  T  S  P  N  S  T  G  C  A  C  P
```

```
421  AGTCCCCATTCCAGTGCCCCAGCCCATACCCCACACCCACGACAAGTTCCATACCC   480
      S  P  H  S  S  A  P  A  I  P  S  P  T  P  T  T  S  S  I  P

481  AGTGCCTAGTCCCCTACCCCGTCCCAATCCACAGTAACACCGAAGTTCACAAGACCGACGT   540
      S  A

541  CGTCGGCCGCTACTCCAGGAGGACCAGTCCTGCTCCGGAGTCGGTGTCACCGGTGTCAGGCC   600

601  AGGCGAACCAAGGGTCGTGGCCTAAGCTTGATCCAATAGAAAGTCATAACAATTTAGTCA   660

661  GTGAGCTCCACGTAAATTATGCATTACAAATAAAGAAAAGTTTGTCTGGCAGTAAAAAAA   720

721  AAAAAAAAAA   730
```

```
  1  GATCGGCACGAGGTCAAGGGAGCCCTCCTTCAGCAACAACAAGCATCGGCAGGTAAGGGA   60
     D  R  H  E  V  K  G  A  L  L  Q  Q  Q  Q  A  S  Q  V  K  G

61  GCCCTCAAGGGAGCAATCAAGGGTGGTCTTCTTCAGCAACAAGCCCAATCCCAAGTCCAA  120
     A  L  K  G  A  I  K  G  G  L  L  Q  Q  Q  A  Q  S  Q  V  Q

121  GGAGCTCTTAAGGGAGCCGTCAAGGGAGCCCTCCTTCAGCAACAACAGGCATCACAGGTC  180
     G  A  L  K  G  A  V  K  G  A  L  L  Q  Q  Q  Q  A  S  Q  V

181  AAGGGAGCCCTCAAGGGAGCCATCAAGGGAGCTCTCCTTCATCAGCAAGCCCAATCCCAA  240
     K  G  A  L  K  G  A  I  K  G  A  L  L  H  Q  Q  A  Q  S  Q

241  TCCCAAGTTCAGGGAGCTCTTAAGGGAGCTG                               271
     S  Q  V  Q  G  A  L  K  G  A
```

FIG. 5

```
1   GGAAGTAGCGAGCATCCGCACTGGGGTCTTTTTGGCTGCATTGCTTTTCTTCTTTCAGC   60
     E  V  A  S  I  R  T  G  V  F  L  A  A  F  F  L  L  S  A

61  GATCCATAACAATGGCCAGTCATGTGTAGATGCAGCCCCCACTCGACGTCCTATGCCATC  120
     I  H  N  N  G  Q  S  C  V  D  A  A  P  T  R  R  P  M  P  S

121 TCCTCCCTGGATGTGCTGGTCCTGGCTGTTTTACTGGTATTGCTACTCTTCTAAGACCTGG  180
     P  P  G  C  A  G  P  G  C  F  T  G  I  A  T  L  L  R  P  G

181 TCAAGGACAGCAACCTGGTCAAGGACAGCAACCTGGTCAAGGCGTCCTCCAATGCCACG    240
     Q  G  Q  Q  P  G  Q  Q  P  G  Q  G  R  P  P  M  P  R

241 TCCAGGACCTGTTCCAGGACATCTGGAACATCACCTCAAGGAAGACCCAATGGAGCACCTCG 300
     P  G  P  V  P  G  T  S  G  S  S  P  Q  G  R  P  N  G  A  P  R

301 TCCAGGACCTGTTCCTGGAACATCACCTCAAGGAAGACCTAACGCAAGACCCTCG       360
     P  G  P  V  P  G  T  S  G  S  S  P  Q  G  R  P  N  A  R  P  R

361 TCCAGGACCTGTTCCTGGAACACCAACTGTATCCCTCCGGATCATCCTCCTGGGTCATC    420
     P  G  P  V  P  G  T  P  T  V  S  S  P  G  S  S  P  G  S  S
```

```
421  TCCAGGAATATCTCTAGGAACGCCCTCTAGGAACACCTCTCAAGGATCACC   480
      P   P   G   I   S   L   G   T   P   L   G   T   P   Q   G   S   P

481  TTTTGGATCATCTCTTGGATCATCGATAGGATCACCTCCTGCAACATCTCCTGGATCATC   540
      F   G   S   S   L   G   S   S   I   G   S   P   P   A   T   S   P   G   S   S

541  TTCTCCCGTCACCTCCTGGATCAGCAGCGAATGTGAACCTGGGTCCTCGACCAATTCGCGG   600
      S   P   P   P   G   S   A   N   V   N   L   G   P   R   P   I   R   G

601  TCCTGGAAGGCATTGACGGGACCAGTTCTGCTGTATTCCTCCGTGCACAATGAGGGAA   660
      P   G   R   H

661  GGCATTGATGGGACCAGTTCTGCTGTGTATTCCTCCGTGCACAGTGAGGGAATCTATCAA   720

721  TAGTGCAATAA   731
```

FIG. 5(CONTD.)

```
  1  GGCTTCGGCAGCCCACTCAGCGGGTTTCGGCAGCCCACTC   60
     G  F  G  S  P  L  S  G  F  G  S  P  L

61  AGCGGGCTTCGGCAGCCCACTCAGCGGGATTCGGGTAGCCCA  120
     S  G  F  G  S  P  L  S  G  F  G  S  P

121  CTCAGCGGGATTCGGGTAGCCCATTCGGCAGCTACGGTCCCC  180
     L  S  G  F  G  S  P  F  G  S  Y  G  P

181  CCCAGGAGATTCCCCGGCGACCTCCGCCTCATCTCTGAGCC  240
     P  R  R  F  P  G  D  L  R  L  I  S  E

241  AGCGATGCCGTCTACACCGCTGTCGTCCAGCCCGTCACAAGC  300
     S  D  A  V  Y  T  A  V  V  Q  P  V  T  S

301  GGTCCCCATGTCACCGGCCAAGTACAGGAACACGTTGCAATC  360
     G  P  H  V  T  G  Q  V  Q  E  H  V  A  I

361  AGCTATATTACGACGGATTAGTCAACACAGTCATCTTAAGCAAAATGTATCTAAAATAAAA  420

421  TTTATCTGCCT  431
```

```
  1  GGAGATCACCTGCTTGCAAAGGACAACGTCCTAACACAGCCGCAAAATGAAAGCTTTCTT   60
                                                        M K A F F

61  CGTTCTTTCCCTTCTTTCAACCCCGCACTGACGAATGCAGCAAGGGCTGGTCGTCTTGG   120
      V L S L L S T A A L T N A A R A G R L G

121  AAGCGACCTGGATACATTTGGAAGGTACACGGTAACCTATATGCCGGCATCGAAAGAGC   180
      S D L D T F G R V H G N L Y A G I E R A

181  TGGCCCTCGTGGATACCCAGGGCTTACCGCATCGGCATCGATTGGAGGCGAAGTGGGTGGCACGACT   240
      G P R G Y P G L T A S I G G E V G A R L

241  CGGTGGTCGTGCCGGTGTGGGAGTGAGCAGCTACGGCTATGGTTACCCTTCATGGGGCTA   300
      G G R A G V G V S S Y G Y G Y P S W G Y

301  TCCGTATGGTGGATACGGTGGATACGGTGGATATGATCAGGG   360
      P Y G G Y G G Y G G Y G G Y D Q G
```

```
361  TTTTGGCTCTGCATACGGCGGCTACCCCGGCTACTACTATCCCAGTGGCTA    420
      F  G  S  A  Y  G  G  Y  P  G  Y  Y  Y  Y  P  S  G  Y

421  CGGTGGGGGCTACGGTGGTAGCTACGGTGGTAGCTACACCTATCCCAA      480
      G  G  Y  G  G  S  Y  G  G  S  Y  T  Y  P  N

481  CGTTCGGGCTTCAGCTGGTGCCGCAGCTTGAGCTTCTCCTTCAGCGTCACAGTAAGAAAT    540
      V  R  A  S  A  G  A  A  A  *

541  CATGGAGCACCCGATCGAGAAATACAGAGGTTCTCAAAAGCGTACGGGATGCCAACCAGC    600

601  AAGAAATTGCGCCGCAAAATGTGTGAGAACAATACAAGTTTTCTGTAAAAAAAAAA       656
```

```
1   ACGGACTAGGTTTCGCTGGCGTCCCTCTTATTGGCGGATACGGCTACGGTCCTTTCGTAG    60
     G  L  G  F  A  G  V  P  L  I  G  G  Y  G  Y  G  P  F  V  G

61  GAGCCTTCGCGTACGGTCTTGTGGGGCCTGGCGGGTATGGCTACCCTGCCTTCGGAC   120
     A  F  A  Y  G  L  W  G  G  L  G  G  Y  G  Y  P  A  F  G  L

121 TCTCCTGGGTTCCACATGGTTTTGGAGGCTTTGGAGCTTCTCCGTCTGCTGCTGGTTTCC  180
     S  W  V  P  H  G  F  G  G  F  G  A  S  P  S  A  A  G  F  R

181 GCTCGCTTTGGAGCCTCTT    199
     S  L  W  S  L
```

FIG. 9

```
R.appendiculatus  GLGFAGVPLIGGYGYGPFVGAFAYGLWGGLGGYGYPAFGLSWVPHGFGGFGASP
                  |:|:|: :::|||||:  :|::::||  : :||||.|:: | :::||:||::
                  GYGY.GAKKVGGYGYGAKLGGYGYG. .AKIGGYGYGAKSGIQV.RALGGYGAGA P.californica
```

EXPRESSION OF RECOMBINANT (TRUNCATED)
STRUCTURAL PROTEIN, 64TRP IN *Escherichia coli* CELLS SDS-PAGE: (A) AND (B) WESTERN BLOT (USING ANTI-64TRP ANTISERUM) AND COOMASSIE BLUE STAINED 15% POLYACRYLAMIDE GEL, RESPECTIVELY OF IPTG-INDUCED *E.coli* CELLS EXPRESSING 64TRP PROTEIN. SAMPLES WERE SOLUBULISED AT 100°C IN SDS PRIOR TO LOADING THE GELS.

FIG. 11a cDNA inferred sequence alignment between the protein sequence of 64P and other related structural proteins.

Sequences are: ker1=keratin complex2 basic protein, ker2=mouse keratin, ker3=mouse epidermalK protein, ker4=human keratin protein, 64P=R. appendiculatus putative structural protein

FIG. 11b cDNA inferred sequence alignment between the protein sequences of 64TRP and other structural proteins.

```
col1   T G A G V G G R L G G G L G A G G R L G G . . . . . . . G L G . . . . . . 121
col64  . N A A R A G R L G G S D L D T F G R V H G . . N L Y A G I E R A G P R G Y P G L T . . 38
col3   A G A G V G G G V S G N V G A G V G V G G L G G A A N G G V G A N A G V G A G 239
col4   G A G G V G G A . . G G L G G L G G L G G L G G A S G L G G L G . . 120
col2   Y P G P T G D Y G Q Q G A P G L P G L D G G I G Y K G Q R G V P G Q E V I Q G E 815 col1   . . . . . . . . . . . . . . . . . . . G G L G G . . G L G G G L G G L R 141
col64  . . . . . . . . . . . . . . . . . . . A S I . G G . E V G A R L G G A V G V S 58
col3   V S G N T G A G V G G G A S G G A N G G V S A N A G V G G . S A G G S V G G 283
col4   . G A S G L G G L G G L G G A G A G G L G G V G G . A G G A G G V G G G 159
col2   G P P G R S G I K G F P G D V G A P G Q Y G L A G R P G P K G V K G E Q G P D G A V G Q T 861
```

Sequences are: col1=Glycine-rich GX protein-motif LGG, col2=collagen type Iv alpha protein, col3=IPIB2 precursor protein, col4=Glycine rich cell wall protein, 64TRP=R. appendiculatus truncated structural protein

FIG. 12b
A
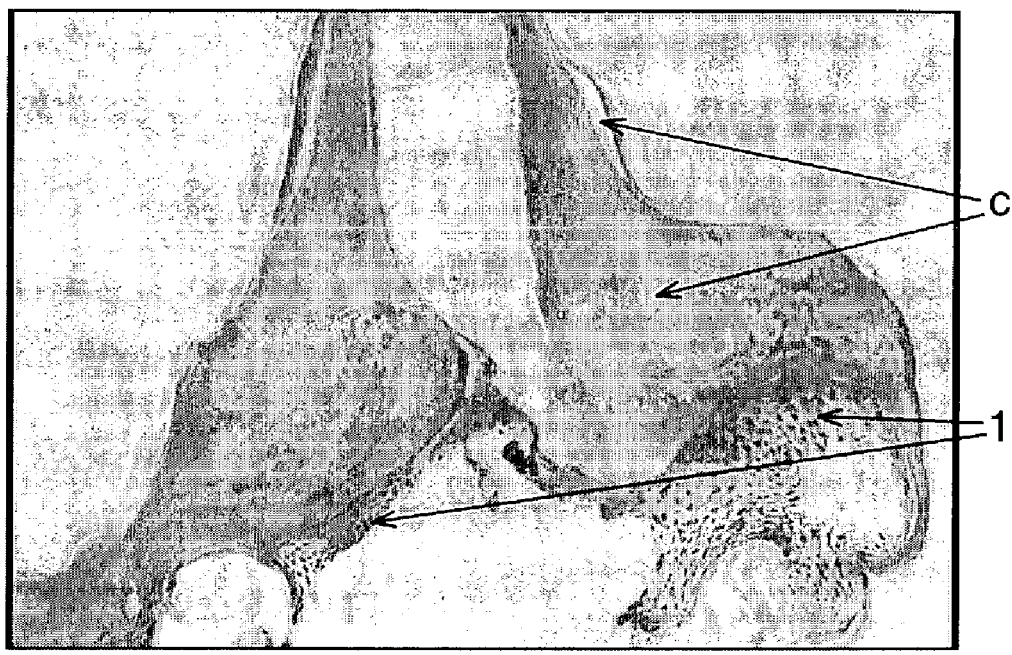
B
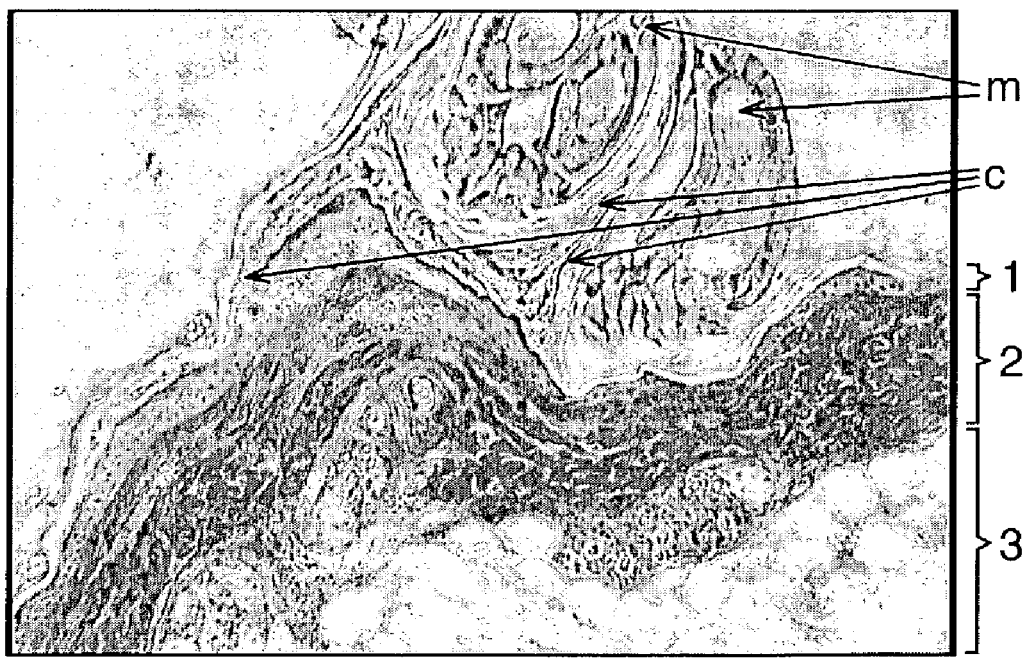

FIG. 13b

SEQUENCE LISTING

```
<160> NUMBER OF SEQ ID NOS: 17

<210> SEQ ID NO 1
<211> LENGTH: 81
<212> TYPE: PRT
<213> ORGANISM: R. appendiculatus

<400> SEQUENCE: 1

Met Lys Ala Phe Val Ala Val Ala Leu Leu Ser Ala Val Ser Val Ala
  1               5                  10                  15

His Ala Ala Leu Lys Thr Asp Val Ala Ser Gly Pro Ala Gly Ser Gly
             20                  25                  30

Ala Leu Ser Leu Gly Val Gly Gly Phe Pro Ser Gly Ala Ser Leu Gly
```

```
                35                  40                  45
Ser Leu Ser Gly Val Thr Leu Ser Gly Ala Gly Ser Ser Val Ser Gly
         50                  55                  60

Arg Pro Gly Ser Pro Gly Ser Ala Gly Pro Ser Ser Gly Pro Ala Val
 65                  70                  75                  80

Ser

<210> SEQ ID NO 2
<211> LENGTH: 267
<212> TYPE: DNA
<213> ORGANISM: R. appendiculatus

<400> SEQUENCE: 2
aaaccaaggc aggacacagc agccatgaag gccttcgttg cagtcgccct tttgtctgca      60
gtttccgtgg cacatgctgc cctcaagact gacgtagcca gtggacctgc cggttctggt     120
gcactaagtc taggagttgg aggcttcccg tccggtgctt cgcttggcag ccttagtggc     180
gtaaccctct ctggtgctgg ctcttccgtg tctggccgcc ctggatcccc tggatcggct     240
ggtcctagct ctggacccgc agtgtcg                                         267

<210> SEQ ID NO 3
<211> LENGTH: 90
<212> TYPE: PRT
<213> ORGANISM: R. appendiculatus

<400> SEQUENCE: 3

Asp Arg His Glu Val Lys Gly Ala Leu Leu Gln Gln Gln Gln Ala Ser
  1               5                  10                  15

Gln Val Lys Gly Ala Leu Lys Gly Ala Ile Lys Gly Gly Leu Leu Gln
             20                  25                  30

Gln Gln Ala Gln Ser Gln Val Gln Gly Ala Leu Lys Gly Ala Val Lys
         35                  40                  45

Gly Ala Leu Leu Gln Gln Gln Gln Ala Ser Gln Val Lys Gly Ala Leu
     50                  55                  60

Lys Gly Ala Ile Lys Val Cys Leu Leu His Gln Gln Ala Gln Ser Gln
 65                  70                  75                  80

Ser Gln Val Gln Gly Ala Leu Lys Gly Ala
             85                  90

<210> SEQ ID NO 4
<211> LENGTH: 731
<212> TYPE: DNA
<213> ORGANISM: R. appendiculatus

<400> SEQUENCE: 4
ggaagtagcg agcatccgca ctggggtctt tttggctgca tttgcttttc ttctttcagc      60
gatccataac aatggccagt catgtgtaga tgcagccccc actcgacgtc ctatgccatc     120
tcctcctgga tgtgctggtc ctggctgttt tactggtatt gctactcttc taagacctgg     180
tcaaggacag caacctggtc aaggacagca acctggtcaa gggcgtcctc caatgccacg     240
tccaggacct gttccaggaa catctggatc acctcaagga agacccaatg gagcacctcg     300
tccaggacct gttcctggaa catctggatc acctcaagga agacctaacg caagacctcg     360
tccaggacct gttcctggaa caccaactgt atcctctccc ggatcatctc tgggtcatc      420 tccaggaata tctctaggaa cgcctctagg aacacctcta ggaacacctc aaggatcacc     480
ttttggatca tctcttggat catcgatagg atcacctcct gcaacatctc ctggatcatc     540
```

-continued

```
ttctccgtca cctcctggat cagcgaatgt gaacctgctg ggtcctcgac caattcgcgg      600
tcctggaagg cattgacggg accagttctg ctgtgtattc ctccgtgcac aatgagggaa      660
ggcattgatg ggaccagttc tgctgtgtat ttctccgtgc acagtgaggg aatctatcaa      720
tagtgcaata a                                                           731
```

<210> SEQ ID NO 5
<211> LENGTH: 730
<212> TYPE: DNA
<213> ORGANISM: R. appendiculatus

<400> SEQUENCE: 5

```
cggacgcaca ctcctgcagg aaggtcatct agttccgcca acatgaagct gctctgtgca       60
ctagccctcg ttgcccttgg acttccattc ggcagcgctt accttggtgg cttcggcggc      120
ctcggtggtt ggggtggcgg tctcggtgcc atctttggcc caggagctta tcccggtttc      180
tatggcctta acagcgtgca cctcttgggc ggcaggttcc accatctctt cgggcgattc      240
ccgccaccac ccggtattgg agctgctgaa gcgcagggga acctaagccc ataccctctt      300
gacatcaaca ccgtccaaga cccgaactgg ccaccccatg gtacgcgttg tctacggcgg      360
agtcttgcgg gagcgcctct gaccctgacc agtcccaatt ccacaggatg tgcctgtccc      420
agtccccatt ccagtgcccc agccataccc agtcccacac ccacgacaag ttccataccc      480
agtgcctagt ccctacccg tcccaatcca cagtaacacc gaagttcaca agaccgacgt      540
cgtcgccgct actccaggag gaccagtcct gctcggagtc ggtgtcaccg gtgtcaggcc      600
aggcgaacca agggtcgtgg cctaagcttg atccaataga aagtcataac aatttagtca      660
gtgagctcca cgtaaattat gcattacaaa taaagaaaag tttgtctggc agtaaaaaaa      720
aaaaaaaaaa                                                              730
```

<210> SEQ ID NO 6
<211> LENGTH: 203
<212> TYPE: PRT
<213> ORGANISM: R. appendiculatus

<400> SEQUENCE: 6

```
Glu Val Ala Ser Ile Arg Thr Gly Val Phe Leu Ala Ala Phe Ala Phe
 1               5                  10                  15

Leu Leu Ser Ala Ile His Asn Asn Gly Gln Ser Cys Val Asp Ala Ala
            20                  25                  30

Pro Thr Arg Arg Pro Met Pro Ser Pro Pro Gly Cys Ala Gly Pro Gly
        35                  40                  45

Cys Phe Thr Gly Ile Ala Thr Leu Leu Arg Pro Gly Gln Gly Gln Gln
    50                  55                  60

Pro Gly Gln Gly Gln Gln Pro Gly Gln Gly Arg Pro Pro Met Pro Arg
65                  70                  75                  80

Pro Gly Pro Val Pro Gly Thr Ser Gly Ser Pro Gln Gly Arg Pro Asn
                85                  90                  95

Gly Ala Pro Arg Pro Gly Pro Val Gly Thr Ser Gly Ser Pro Gln
            100                 105                 110

Gly Arg Pro Asn Ala Arg Pro Arg Pro Gly Pro Val Pro Gly Thr Pro
        115                 120                 125

Thr Val Ser Ser Pro Gly Ser Ser Pro Gly Ser Ser Pro Gly Ile Ser
    130                 135                 140

Leu Gly Thr Pro Leu Gly Thr Pro Leu Gly Thr Pro Gln Gly Ser Pro
```

```
                145                 150                 155                 160
Phe Gly Ser Ser Leu Gly Ser Ser Ile Gly Ser Pro Pro Ala Thr Ser
                    165                 170                 175
Pro Gly Ser Ser Ser Pro Ser Pro Gly Ser Ala Asn Val Asn Leu
            180                 185                 190
Leu Gly Pro Arg Pro Ile Arg Gly Pro Gly Arg
        195                 200
```

<210> SEQ ID NO 7
<211> LENGTH: 199
<212> TYPE: DNA
<213> ORGANISM: R. appendiculatus

<400> SEQUENCE: 7

```
acggactagg tttcgctggc gtccctctta ttggcggata cggctacggt cctttcgtag      60
gagccttcgc gtacggcttg tggggtggcc tcggtggcta tggctaccct gccttcggac     120
tctcctgggt tccacatggt tttggaggct ttggagcttc ccgtctgct gctggtttcc      180
gctcgctttg agcctctt                                                    199
```

<210> SEQ ID NO 8
<211> LENGTH: 54
<212> TYPE: PRT
<213> ORGANISM: R. appendiculatus

<400> SEQUENCE: 8

```
Gly Leu Gly Phe Ala Gly Val Pro Leu Ile Gly Gly Tyr Gly Tyr Gly
 1               5                  10                  15
Pro Phe Val Gly Ala Phe Ala Tyr Gly Leu Trp Gly Gly Leu Gly Gly
            20                  25                  30
Tyr Gly Tyr Pro Ala Phe Gly Leu Ser Trp Val Pro His Gly Phe Gly
        35                  40                  45
Gly Phe Gly Ala Ser Pro
    50
```

<210> SEQ ID NO 9
<211> LENGTH: 50
<212> TYPE: PRT
<213> ORGANISM: P. californica

<400> SEQUENCE: 9

```
Gly Tyr Gly Tyr Gly Ala Lys Lys Val Gly Gly Tyr Gly Tyr Gly Ala
 1               5                  10                  15
Lys Leu Gly Gly Tyr Gly Tyr Gly Ala Lys Ile Gly Gly Tyr Gly Tyr
            20                  25                  30
Gly Ala Lys Ser Gly Ile Gln Val Arg Ala Leu Gly Gly Tyr Gly Ala
        35                  40                  45
Gly Ala
    50
```

<210> SEQ ID NO 10
<211> LENGTH: 199
<212> TYPE: PRT
<213> ORGANISM: R. appendiculatus

<400> SEQUENCE: 10

```
Ala Cys Gly Gly Ala Cys Thr Ala Gly Gly Thr Thr Thr Cys Gly Cys
 1               5                  10                  15
Thr Gly Gly Cys Gly Thr Cys Cys Cys Thr Cys Thr Thr Ala Thr Thr
```

-continued

```
            20                  25                  30

Gly Gly Cys Gly Gly Ala Thr Ala Cys Gly Gly Cys Thr Ala Cys Gly
        35                  40                  45

Gly Thr Cys Cys Thr Thr Thr Cys Gly Thr Ala Gly Gly Ala Gly Cys
    50                  55                  60

Cys Thr Thr Cys Gly Cys Gly Thr Ala Cys Gly Gly Cys Thr Thr Gly
65                  70                  75                  80

Thr Gly Gly Gly Gly Thr Gly Gly Cys Cys Thr Cys Gly Gly Thr Gly
                85                  90                  95

Gly Cys Thr Ala Thr Gly Gly Cys Thr Ala Cys Cys Cys Thr Gly Cys
            100                 105                 110

Cys Thr Thr Cys Gly Gly Ala Cys Thr Cys Thr Cys Cys Thr Gly Gly
        115                 120                 125

Gly Thr Thr Cys Cys Ala Cys Ala Thr Gly Gly Thr Thr Thr Thr Gly
    130                 135                 140

Gly Ala Gly Gly Cys Thr Thr Thr Gly Gly Ala Gly Cys Thr Thr Cys
145                 150                 155                 160
Thr Cys Cys Gly Thr Cys Thr Gly Cys Thr Gly Cys Thr Gly Gly Thr
                165                 170                 175

Thr Thr Cys Cys Gly Cys Thr Cys Gly Cys Thr Thr Thr Gly Gly Ala
            180                 185                 190

Gly Cys Cys Thr Cys Thr Thr
        195
```

<210> SEQ ID NO 11
<211> LENGTH: 148
<212> TYPE: PRT
<213> ORGANISM: R. appendiculatus

<400> SEQUENCE: 11

```
Met Lys Leu Leu Cys Ala Leu Ala Leu Val Ala Leu Gly Leu Pro Phe
1               5                   10                  15

Gly Ser Ala Tyr Leu Gly Gly Phe Gly Gly Leu Gly Gly Trp Gly Gly
            20                  25                  30

Gly Leu Gly Ala Ile Phe Gly Pro Gly Ala Tyr Pro Gly Phe Tyr Gly
        35                  40                  45

Leu Asn Ser Val His Leu Leu Gly Gly Arg Phe His His Leu Phe Gly
    50                  55                  60

Arg Phe Pro Pro Pro Pro Gly Ile Gly Ala Ala Glu Ala Gln Gly Asn
65                  70                  75                  80

Leu Ser Pro Tyr Pro Leu Asp Ile Asn Thr Val Gln Asp Pro Asn Trp
                85                  90                  95

Pro Pro His Gly Thr Arg Cys Leu Arg Arg Ser Leu Ala Gly Ala Pro
            100                 105                 110

Leu Thr Leu Thr Ser Pro Asn Ser Thr Gly Cys Ala Cys Pro Ser Pro
        115                 120                 125

His Ser Ser Ala Pro Ala Ile Pro Ser Pro Thr Pro Thr Thr Ser Ser
    130                 135                 140

Ile Pro Ser Ala
145
```

<210> SEQ ID NO 12
<211> LENGTH: 271
<212> TYPE: DNA
<213> ORGANISM: R. appendiculatus

<400> SEQUENCE: 12

```
gatcggcacg aggtcaaggg agccctcctt cagcaacaac aagcatcgca ggttaaggga      60
gccctcaagg gagcaatcaa gggtggtctt cttcagcaac aagcccaatc ccaagtccaa     120
ggagctctta agggagccgt caagggagcc ctccttcagc aacaacaggc atcacaggtc     180
aagggagccc tcaagggagc catcaaggtc tgtctccttc atcagcaagc ccaatcccaa     240
tcccaagttc agggagctct aagggagctg                                      271
```

<210> SEQ ID NO 13
<211> LENGTH: 431
<212> TYPE: DNA
<213> ORGANISM: R. appendiculatus

<400> SEQUENCE: 13

```
ggcttcggca gcccactcag cggtttcggc agcccactca gcggtttcgg cagcccactc      60
agcggcttcg gcagcccact cagcggattc ggtagcccac tcagcggatt cggtagccca     120
ctcagcggat tcggtagccc attcggcagc tacggtcccc tgtccatggg tctcggagcc     180
cccaggagat tccccggcga cctccgcctc atctctgagc ccacctcccg ccttcccgtt     240
agcgatgccg tctacaccgc tgtcgtccag cccgtcacaa gcgcagtggt ccacaccgag     300
ggtccccatg tcaccggcca agtacaggaa cacgttgcaa tctaagcttt tctaaccgca     360
agctatatta cgacggatta gtcaacacag tcatcttaag caaatgtatc taaaataaaa     420
tttatctgcc t                                                         431
```

<210> SEQ ID NO 14
<211> LENGTH: 114
<212> TYPE: PRT
<213> ORGANISM: R. appendiculatus

<400> SEQUENCE: 14

```
Gly Phe Gly Ser Pro Leu Ser Gly Phe Gly Ser Pro Leu Ser Gly Phe
  1               5                  10                  15

Gly Ser Pro Leu Ser Gly Phe Gly Ser Pro Leu Ser Gly Phe Gly Ser
                 20                  25                  30

Pro Leu Ser Gly Phe Gly Ser Pro Leu Ser Gly Phe Gly Ser Pro Phe
             35                  40                  45

Gly Ser Tyr Gly Pro Leu Ser Met Gly Leu Gly Ala Pro Arg Arg Phe
         50                  55                  60

Pro Gly Asp Leu Arg Leu Ile Ser Glu Pro Thr Ser Arg Leu Pro Val
 65                  70                  75                  80

Ser Asp Ala Val Tyr Thr Ala Val Val Gln Pro Val Thr Ser Ala Val
                 85                  90                  95

Val His Thr Glu Gly Pro His Val Thr Gly Gln Val Gln Glu His Val
            100                 105                 110

Ala Ile
```

<210> SEQ ID NO 15
<211> LENGTH: 656
<212> TYPE: DNA
<213> ORGANISM: R. appendiculatus

<400> SEQUENCE: 15

```
ggagatcacc tgcttgcaaa ggacaacgtc ctaacacagc cgcaaaatga aagctttctt      60
cgttctttcc cttctttcaa ccgccgcact gacgaatgca gcaagggctg gtcgtcttgg     120
```

```
aagcgacctg gatacatttg aagggtaca cggtaaccta tatgccggca tcgaaagagc      180
tggccctcgt ggatacccag ggcttaccgc atcgattgga ggcgaagtgg gtgcacgact     240
cggtggtcgt gccggtgtgg gagtgagcag ctacggctat ggttacccct catggggcta    300
tccgtatggt ggatacggtg gatacggtgg atacggtgga tacggtggat atgatcaggg    360
ttttggctct gcatacggcg gctaccccgg ctactatggc tactactatc ccagtggcta    420 cggtggggc  tacggtggta gctacggtgg cagctacggt ggtagctaca cctatcccaa     480
cgttcgggct tcagctggtg ccgcagcttg agcttctcct tcagcgtcac agtaagaaat     540
catggagcac ccgatcgaga atacagagg  ttctcaaaag cgtacgggat gccaaccagc     600
aagaaattgc gccgcaaaat gttgagaaca atacaagtt  ttctgtaaaa aaaaaa         656
```

<210> SEQ ID NO 16
<211> LENGTH: 154
<212> TYPE: PRT
<213> ORGANISM: R. appendiculatus

<400> SEQUENCE: 16

```
Met Lys Ala Phe Phe Val Leu Ser Leu Leu Ser Thr Ala Ala Leu Thr
  1               5                  10                  15

Asn Ala Ala Arg Ala Gly Arg Leu Gly Ser Asp Leu Asp Thr Phe Gly
             20                  25                  30

Arg Val His Gly Asn Leu Tyr Ala Gly Ile Glu Arg Ala Gly Pro Arg
         35                  40                  45

Gly Tyr Pro Gly Leu Thr Ala Ser Ile Gly Gly Glu Val Gly Ala Arg
     50                  55                  60

Leu Gly Gly Arg Ala Gly Val Gly Val Ser Ser Tyr Gly Tyr Gly Tyr
 65                  70                  75                  80

Pro Ser Trp Gly Tyr Pro Tyr Gly Gly Tyr Gly Gly Tyr Gly Gly Tyr
                 85                  90                  95

Gly Gly Tyr Gly Gly Tyr Asp Gln Gly Phe Gly Ser Ala Tyr Gly Gly
            100                 105                 110

Tyr Pro Gly Tyr Tyr Gly Tyr Tyr Pro Ser Gly Tyr Gly Gly Gly
        115                 120                 125

Tyr Gly Gly Ser Tyr Gly Gly Ser Tyr Gly Gly Ser Tyr Thr Tyr Pro
    130                 135                 140

Asn Val Arg Ala Ser Ala Gly Ala Ala Ala
145                 150
```

<210> SEQ ID NO 17
<211> LENGTH: 65
<212> TYPE: PRT
<213> ORGANISM: R. appendiculatus

<400> SEQUENCE: 17

```
Gly Leu Gly Phe Ala Gly Val Pro Leu Ile Gly Tyr Gly Tyr Gly
  1               5                  10                  15

Pro Phe Val Gly Ala Phe Ala Tyr Gly Leu Trp Gly Gly Leu Gly Gly
             20                  25                  30

Tyr Gly Tyr Pro Ala Phe Gly Leu Ser Trp Val Pro His Gly Phe Gly
         35                  40                  45

Gly Phe Gly Ala Ser Pro Ser Ala Ala Gly Phe Arg Ser Leu Trp Ser
     50                  55                  60

Leu
 65
```

TISSUE CEMENT PROTEINS FROM *RHIPICEPHALUS APPENDICULATUS*

STATEMENT REGARDING RELATED APPLICATIONS

The application is a continuation of U.S. Ser. No. 09/554,547 filed 7 Jul. 2000 (now abandoned), which is a National Phase application of PCT/GB98/03397, filed 12 Nov. 1998, which claims priority to GB 9723945.3 filed 12 Nov. 1997, which applications are herein specifically incorporated by reference in there entireties.

The present invention relates to tissue cement proteins produced by certain species of blood-feeding ectoparasites. These proteins and compositions comprising these proteins are particularly useful for the temporary or permanent bonding of animal tissues to each other or to other biomaterials. The present invention also relates to the use of tissue cement proteins in the production of vaccines that protect animals against the bite of blood-sucking ectoparasites and the transmission of viruses, bacteria and other pathogens by such ectoparasites Cement is produced by many blood-feeding ectoparasites, including certain species of Ixodid ticks Ixodid (hard) ticks are haematophagous parasites that attach themselves to a vertebrate host by means of a 'cement cone', a product of the type II and type III acini of the tick salivary glands (Kemp et al., 1982. Walker et al., 1985) (All documents referred to herein are listed at the end of the description.)

The cement that forms the cone is a milky-white secretion that is injected into the skin of animals on which these parasites feed. The cement comprises a number of interacting protein and carbohydrate components. The cement spreads into the bite site and over the skin and, upon hardening, ensures that the mouthparts remain firmly anchored to the host during the feeding period, which typically lasts 4 to 8 days. The cement cone functions additionally as a gasket to prevent leakage of fluids from the bite site during feeding.

The tick cement cone is a layered structure, constructed from two major types of cement. The first type of cement is produced just minutes after establishing the bite site and hardens quickly to form a rigid 'core' of the cone. A second type of cement is secreted later, about 24 hours after attachment, and hardens more slowly to form a more flexible 'cortex'. In adult ticks, cement production typically continues until the 3rd or 4th day after attachment (Kemp et al., 1982; Sonenshine et al., 1991).

The tick cement cone appears to be mainly proteinaceous, but also contains some carbohydrate and lipid. An early study found the amino-acid composition of whole cement in *Boophilus microplus* to be rich in glycine, leucine, serine and tyrosine (Kemp et al., 1982) However, the individual proteins comprising the tick cement are very poorly characterised Although the mobility of the component proteins has been show on SDS-PAGE gels, none have yet been purified The process by which the cement components harden is also not understood, although mechanisms similar to the tanning of cuticle and coagulation of haemolymph have been proposed (Kemp et al., 1982; Moorhouse and Tatchell, 1966). At present no direct scientific evidence has been produced to substantiate these theoretical mechanisms.

It has been noted that the polypeptides that form the cement cortex appear to be similar to certain structural components of vertebrate skin, involvement of these vertebrate-like molecules may enable ticks to use host-derived enzymes during the cement hardening process, for example lysyl oxidases which cross-link collagen and elastin (Siegel, 1979); or transglutaminases, such as the coagulation factor XIIIa, which is induced during wound healing and cross-links fibronectin, fibrins and collagen (Ichinose et al., 1990). These enzymes may cross-link cortex polypeptides to the extracellular matrix proteins of the skin.

Other enzymes such as phenoloxidases or peroxidases which catalyse the hardening of arthropod extracellular structures (Sugumaran et al., 1992) have been identified in *R. appendiculatus* salivary glands and are therefore likely to play a role in solidifying the cement cone.

The composition of tick cement appears to be similar amongst different Ixodid tick species For example, an antiserum raised against a 90 kD salivary protein of the brown ear tick, *Rhipicephalus appendiculatus*, has been shown to recognise polypeptides from the salivary glands and cement proteins of the American dog tick, *Dermacenter variabilis*, the lone star tick, *Amblyomma americanum*, and the brown dog tick, *R sanguineus* (Jaworski et al., 1992)

All these tick species are extremely effective as transmitters of disease For example, *R appendiculatus* represents a major obstacle to livestock development in several sub-saharan regions It transmits the protozoan parasite *Theileria parva* which causes the usually fatal East Coast Fever This disease is often considered the most important disease of cattle (Norval et al., 1992a, Norval et al., 1992b). This tick is also the main vector of the virus causing Nairobi sheep disease, a disabling and often deadly disease in sheep and goats (Davies. 1988). *R. appendiculatus* and other tick pests also cause considerable damage to the skin, thereby affecting the leather industry.

In an effort to combat parasite-transmitted diseases, unpurified cement components have been tested as inducers of host resistance (Brown et al., 1986; Shapiro et al., 1989), but reliable vaccines based on cement proteins have not been successfully developed. Cone proteins would appear to be a reasonable target for a vaccine since the formation of the cone is essential for the tick to attach to the host and feed. However, only some of the cone proteins are antigenic.

There therefore exists a great need for an effective vaccine to combat diseases that are transmitted by blood-feeding ectoparasites. The elucidation of the components of tissue cement produced by these organisms would allow the rational design of such vaccines.

Furthermore, these molecules would prove useful in medicine as components of tissue cement. Presently available tissue cements are of two types, both of which suffer from significant disadvantages. Acrylic-based glues are extremely strong, yet are also very toxic and can thus only be used in very small quantities in the body. The second type of tissue cement used is non-immunogenic but forms a much less strong bond. Consequently this type of cement is only useful in a small number of surgical procedures. There is thus a great need for a non-immunogenic tissue cement that is capable of bonding mammalian tissue with great strength.

SUMMARY OF THE INVENTION

According to the present invention there is provided a tissue cement protein having the amino acid sequence shown in FIG. 3 (SEQ ID NO: 11) or FIG. 7 (SEQ ID NO: 16) or containing any one of the partial amino acid sequences shown in any one of FIGS. 2 (SEQ ID NO: 1), 4 to 6 (SEQ ID NOS: 3, 6 and 14) and 8 (SEQ ID NO: 17), related tissue cement proteins from blood-feeding parasites, preferably ticks, and functional equivalents thereof.

The proteins of the present invention are of two subtypes: group A and group B. Proteins in group A form the cement cone core when secreted in saliva and harden quickly to form a rigid latex-like structure. The proteins in group B form the cortex of the cement cone and harden more slowly. The resulting structure is more flexible. Accordingly, functional equivalents of proteins of either group A or group B will possess these respective activities and properties The term "functional equivalents" is used herein to describe those proteins that have an analogous function to tissue cement proteins containing the amino acid sequences identified in any one of FIGS. 2 to 8 (SEQ ID NOS: 1, 3, 6, 11, 14, 16 or 17).

These proteins may belong to the same protein family as the proteins and partial proteins identified in FIGS. 2 to 8 (SEQ ID NOS: 1, 3, 6, 11, 14, 16 or 17). By protein family is meant a group of polypeptides that share a common function and exhibit common sequence homology between motifs present in the polypeptide sequences.

By sequence homology is meant that the polypeptide sequences are related by divergence from a common ancestor. In particular, as is discussed in more detail below, the proteins and partial proteins identified herein possess certain sequences in common that are repeated several times throughout the sequence of the protein. Preferably, the homology between polypeptide sequences is at least 50% across the whole of the amino acid sequence of the protein. More preferably, the homology is at least 75% across the whole of the amino acid sequence of the protein. Most preferably, homology is greater than 80% across the whole of the protein sequence.

By "analogous function" is meant firstly that the proteins have retained the capacity to form a cement Such proteins will thus be capable of hardening over a period of time to form a solid mass or glue. Secondly, this term may refer to proteins that are structurally similar to group A or group B proteins and thus contain similar or identical epitopes These functional equivalents may thus be used as immunogens to develop vaccines, directed against blood-feeding parasites, that target members of the tissue cement protein family Functional equivalents of tissue cement proteins may include, for example, mutants containing amino acid substitutions, insertions or deletions from the wild type sequence Functional equivalents with improved function from that of the wild type sequence may also be designed through the systematic or directed mutation of specific residues in the protein sequence. Improvements in function that may be desired will include greater strength of bonding, faster speed of bonding or greater flexibility of the hardened cement Functional equivalents of tissue cement proteins or protein fragments may be made more or less immunogenic than the corresponding wild type protein or protein fragment in order to suit a desired application. If the proteins are to be used in surgical procedures as tissue cements then the proteins should ideally be non-immunogenic to evade attack by the immune system. However, if the tissue cement proteins are to be used in a vaccination regime to induce host resistance to parasite proteins, then the proteins may be modified so as to enhance their immunogenicity. They will thus be more likely to elicit an immune response in the vaccinated host.

Functional equivalents will include conservative amino acid substitutions that do not affect the function or activity of the protein in an adverse manner. This term is also intended to include natural biological variants (e.g. allelic variants or geographical variations within the species from which the tissue cement proteins are derived).

According to the invention, fragments of tissue cement proteins are also envisioned as functional equivalents. Fragments that have retained those portions of the protein that are responsible for a desired activity may prove ideal in certain applications. For example, short stretches of peptide derived from immunogenic portions of tissue cement proteins will be useful as immunogens. An antibody will normally recognise an epitope comprising between six and twelve amino acid residues. Such short stretches of polypeptide sequence are simple to produce in large quantities, either synthetically or through recombinant means The tissue cement proteins of the present invention may function either as a structural component of tissue cement or may possess an enzymatic activity directed against the structural components of the tissue cement.

It is thought that most of the protein and partial protein sequences so far identified and shown in FIGS. 2 to 8 (SEQ ID NOS: 1, 3, 6, 11, 14, 16 or 17) are structural components of tissue cement. The applicant, however, does not wish to be bound by this theory. For example, the protein sequence identified in FIG. 2 (SEQ ID NO: 1) appears to contain a signal sequence and its sequence resembles that of keratin, a widely studied structural protein. Similarly, the protein whose sequence is set out in FIG. 3 (SEQ ID NO: 11) also contains a signal sequence and is glycine and proline rich, like many structural proteins. The cemA protein, whose partial sequence is illustrated in FIG. 4 (SEQ ID NOS: 3), contains a number of repeats and is thus also likely to be a structural component of tissue cement.

The protein of FIG. 5 (SEQ ID NO: 6) is composed of a number of repeats and resembles collagen in sequence. The encoding cDNA shares sequences in common with glutenin, a known self-assembling protein. It thus seems likely that this protein is capable of self-assembly. The applicant, however, does not wish to be bound by this theory. The possibility that this particular sequence may be involved in self-assembly raises the opportunity of using these motifs to bestow on an unrelated protein the ability to self-assemble.

In common with some of the other proteins illustrated in the accompanying Figures, the protein of FIG. 6 (SEQ ID NO: 14) contains a number of consensus recognition sites for carbohydrate moieties, in particular glycosaminoglycans The protein sequence illustrated in FIG. 7 (SEQ ID NO: 16) also contains consensus attachment sites for glycosaminoglycan moieties and possesses a putative signal sequence. The amino terminal half of the protein resembles collagen, whilst the carboxy terminal shares more in common with keratin. The protein is glycine-rich and contains several repeats of the motif (C/S)1-4(Y/F) which is also found in structural proteins from the egg shells of certain insects. The tyrosines in these consensus sequences may be involved in the cross-linking of this protein through the formation of dityrosine bridges by the action of phenoloxidases.

The sequence of FIG. 8 (SEQ ID NO: 17) is both glycine and tyrosine rich and resembles a cement protein of the reef-building polychaete *Pragmatopoma californica* (see FIG. 9) (SEQ ID NOS: 9). It is thus likely that this protein is also a structural component of tissue cement. The applicant, however, does not wish to be bound by this theory.

The enzymatic activity that may be possessed by the tissue cement proteins of the present invention may involve the ability to effect such covalent modifications as phosphorylation, glycosylation, reduction or oxidation of other proteins and carbohydrate moieties and may result in the cross-linking of the structural components of the tissue cement. Cross-linking may be either reversible or irreversible and may occur between homologous or heterologous components of the tissue cement. The cross-linking may also occur between tissue cement proteins and non-parasite proteins such as, for example, components of vertebrate tissue.

The tissue cement proteins of the present invention may be group A proteins. By "group A" is meant that in parasite saliva these proteins form the core of the cement cone. The function of the cone core in parasites is to attach to the skin of a vertebrate host and to form a rigid bond that will not break easily. Accordingly, these proteins form a hard latex-like cement that sets and bonds to the vertebrate skin quickly. Group A proteins are thus ideally suited to applications that require a quick-setting tough bond.

The tissue cement proteins or the present invention may be group B proteins. By "group B" is meant that in tick saliva these proteins form the cortex of the cement cone One function of the cortex in parasites is to form a gasket-like seal around the bite site, to prevent leakage of fluids. A further function of the cortex proteins is to form a flexible hinge so that the parasite will not be easily brushed off its host. Accordingly, group B proteins harden more slowly than group A proteins, but set to form a more flexible, plant cement These proteins are thus ideally suited for applications when a more flexible bond is required.

Many of the structural tissue cement proteins of the present invention share in common the ability to bind to vertebrate tissue. This binding may be due to an inherent affinity possessed by the protein for certain components of the vertebrate skin, such as collagen. However, an affinity for vertebrate proteins may only manifest itself when in the presence of enzymes whose activity is required in order to generate an association between a tissue cement protein and a component of the skin. This enzymatic activity may be derived from tissue cement proteins themselves or may be provided by enzyme components of the vertebrate skin, such as lysyl oxidases, that cross-link collagen and elastin or transglutaminases, such as the coagulation factor XIIIa, that cross-link fibronectin, fibrins and collagen during many vertebrate heating processes.

The tissue cement proteins or their functional equivalents according to the present invention may be derived from any blood-feeding parasite. Preferably, the tissue cement proteins of the present invention are derived from blood-feeding ectoparasites, more preferably ticks. Most preferably, the tissue cement proteins of the present invention are derived from the brown ear tick *Rhipicephalus appendiculatus.*

The tissue cement proteins of the present invention may also comprise carbohydrate components. Many tissue cement proteins are in fact glycoproteins, containing carbohydrate attachments covalently bound at various sites in the protein. The carbohydrate generally will comprise a series of monosaccharide units that commonly occur as an oligosaccharide or fairly small polysaccharide As has been discussed briefly above, many of the proteins so far identified in ticks possess consensus attachment sites for glycosaminoglycans (glycans containing aminosaccharide residues)

The tissue cement proteins of the invention may be present in the tissue cement as monomers, dimers, tetramers, or as oligomers comprising a number of homologous or heterologous monomers as one unit. This is particularly true of structural tissue cement proteins, which may associate non-covalently as part of the cement hardening process. The applicant, however, does not wish to be bound by this theory.

The tissue cement proteins of the present invention may be purified from cement produced by live parasites. This may be done by treating collected cones with a wash solution such as PBS, a TRIS buffer or non-ionic detergents, for example Tween-20 or Triton. Cement proteins may be prepared through immunoprecipitation using antibodies that are specific for epitopes in the protein sequence. Alternatively, the proteins may be prepared synthetically, or using techniques of genetic engineering. Preferably, the tissue cement proteins of the present invention comprise recombinant polypeptides produced by expression from an encoding nucleic acid.

Synthetic molecules designed to mimic the tertiary structure or active site of the tissue cement proteins constitute a further aspect of the invention.

A further aspect of the present invention comprises tissue cement proteins that are fused to other molecules such as labels, toxins or bioactive molecules. Particularly suitable candidates for fusion will be reporter molecules such as luciferase, green fluorescent protein or horse radish peroxidase. Linker molecules such as streptavidin or biotin may also be used. Additionally, bioactive peptides or polypeptides may be fused to a tissue cement protein Such molecules may comprise molecules with antiseptic or antibiotic properties, or toxins for targeting to cancer cells.

The proteins may be fused chemically, using methods such as chemical cross-linking. Such methods will be well known to those of skill in the art and may comprise, for example, cross-linking of the thiol groups of cysteine residues. Chemical cross-linking will in most instances be used to fuse tissue cement proteins to non-protein molecules, such as labels The labels may be radiolabels or labels that can be detected spectroscopically, for example fluorescent or phosphorescent chemical groups When it is desired to fuse a tissue cement protein to another protein molecule, the method of choice will often be to fuse the molecules genetically In order to generate a recombinant fusion protein, the genes or gene portions that encode the proteins or protein fragments of interest are engineered so as to form one contiguous gene arranged so that the codons of the two gene sequences are transcribed in frame.

A tissue cement protein may be fused genetically to any protein for which the encoding gene sequence is or becomes known. Particularly suitable candidates for fusion will be reporter molecules such as luciferase, green fluorescent protein, biotin, avidin, streptavidin or horse radish peroxidase. Additionally, toxin peptides or polypeptides may be fused to a tissue cement protein. Antiseptic or antibiotic proteins and peptides may also be fused to the tissue cement proteins of the present invention.

According to a further aspect of the present invention there is provided a pharmaceutical composition comprising a tissue cement comprising a mixture of group A and group B tissue cement proteins in the absence of other parasite saliva proteins, optionally in the presence of one or more compounds capable of cross-linking said tissue cement proteins, in conjunction with a pharmaceutically-acceptable excipient Such a pharmaceutical composition has many applications, particularly in skin surgery and wound healing, for the temporary or permanent bonding of human or animal tissues to each other or to other biomaterials.

Tissue cement has previously been used in surgical procedures to provide adhesion and stability to living tissues to enable the normal processes of healing and repair to take place or to provide a long term bond in situations where normal healing is delayed or unlikely to occur Tissue cement formed from the proteins of the present invention have several advantages over conventional tissue cements For example, the proteins of the invention form strong bonds with vertebrate tissues. This makes them ideal for use as components of a tissue cement to bond two tissue surfaces or edges together Different surgical procedures necessitate the use of tissue cement with different properties. Tissue cement formed from the proteins of the present invention is therefore ideal, since the hardening or elastic properties of the cement may be tailored precisely to provide the particular requirements of the surgical procedure through modification of the relative amounts of group A and group B proteins that the cement comprises. The tissue cement is in this manner extremely versatile.

Tissue cement with a high content of group A proteins will generally be useful for procedures that require an extremely tough bond that will not need to flex to any great extent A good example of such a bond might be a bond between two bone surfaces or between a bone surface and the surface of an artificial joint. A high group A content tissue cement will also be required when it is necessary that the bond sets quickly.

For procedures such as the bonding of skin lacerations, where a high degree of flexibility is required, a tissue cement will be used that contains a high content of group B proteins. However, group B proteins do bond more slowly, so tissue cement with a high group B content will not generally be used for procedures that require a tough bond to form rapidly. However, this cement may be used in conjunction with other measures, such as surgical staples or group A tissue cement, that can form a quick bond to hold the tissues together while the group B proteins harden.

Pharmaceutical compositions that comprise tissue cement proteins according to the present invention may also contain additional preservatives, or components responsible for the prevention of premature setting. The composition may also comprise a propellant, for instance, if the tissue cement is to be sprayed onto tissue surfaces. Such compounds will be well known to those of skill in the art.

One important advantage of the tissue cement proteins of the present invention is that, in situ in vertebrate tissue these proteins are non-immunogenic and therefore do not cause inflammation of the tissue. This is particularly relevant when the tissue cement is intended for internal use, for example in the securing of prolapsed organs. Were the tissue cement immunogenic, an immune attack would be directed against the tissue cement, so causing local inflammation, disrupting the cement and preventing the permanent bonding of the tissue.

The current rationale in surgery to overcome immune rejection involves combatting the initial rejection phenomena until, eventually, the immune system becomes tolerant. For example, after organ transplants, huge combined doses of immunosuppressive agents are initially required that are gradually reduced during treatment until, if the transplant successfully survives for a year or so, very little maintenance immunotherapy is required.

The tissue cement proteins of the present invention can also be used to prevent immune rejection. Aside from their natural non-immunogenicity, another property of the tissue cement proteins of the present invention is that the proteins themselves bind to bioactive proteins in the saliva of an ectoparasite, such as tick histamine-binding proteins. By doing this, the cement proteins localise the action of the various immunosuppressive molecules produced by the organism. These immunosuppressive compounds alter over time during the course of feeding in order to adapt to the host's rejection response. Hence the cement cone, in effect, is an active local immunosuppressive structure.

The ability to bind to bioactive parasite proteins means that tissue cement comprising tissue cement proteins according to the present invention may be complemented with certain immunosuppressive molecules produced by some parasites. For example, suitable molecules might include vasoactive amine binding molecules that are the subject of co-pending International patent application PCT/GB97/01372 These molecules will bind to the tissue cement, and so provide a local immunosuppressive structure that will disguise any allogeneic or even xenogeneic organ and prevent its rejection.

These properties of the tissue cement proteins of the present invention thus provide an addition to the conventional uses of tissue cement to hold articulated joints to bone or to repair damaged organs. Aside from its use as a non-immunogenic adhesive, tissue cement produced according to the present invention may be used as an adjunct to organ transplantation to supply and localise immunosuppressive compounds to the locality of the transplant A further aspect of the present invention is therefore to provide tissue cement with immunosuppressive properties by complementation of the basic cement with one or more tissue cement proteins of the present invention, optionally in conjunction with parasite-derived immunosuppressive compounds.

Other specific applications of tissue cement formed from the tissue cement proteins of the present invention may include, but will not be confined to, those given in the following list:

repair of incised surgical wounds in place of conventional closures such as sutures or staples; repair of lacerations such as perineal tears following childbirth or flap lacerations after trauma; the grafting of skin, cultured skin substitutes or biomaterial substitutes to chronic wounds, burns, skin graft donor sites and in reconstructive or cosmetic plastic surgery; the securing of myoplastic flaps; tissue to tissue repair such as repair of lacerations of the liver or other parenchymatous organs; tissue to tissue anastomosis such as gastrointestinal anastomosis or tissue to biomaterial anastomosis such as vascular repair or anastomosis; tissue to tissue reconstruction such as the securing of prolapsed organs in their anatomical site; tissue to tissue approximation as in pleuro-pleural adhesion following recurrent pneumothorax; as a sclerosant in procedures such as the injection of haemorrhoids; in neurosurgical procedures such as the repair or patching of dura mater with natural or artificial substitutes and the grafting or repair of severed neural tissue; in orthodontic procedures such as the reimplantation of teeth or the reconstruction of the mandibular or maxillary arches using bone chips or materials such as collagen matrices or hydroxyapatite: in orthopaedic procedures including vertebral fusion, arthrodesis, fixation of fractions and osteotomies and the implantation of prostheses such as hip arthroplasty; in procedures such as rhytidectomy where the use of sutures is undesirable on cosmetic grounds; securing of artificial materials such as Marlex™ mesh in hernioplasty (performed in open operation or endoscopically); repair of friable tissue such as tendon or muscle; as a haemostat on oozing surfaces or in circumstances where haemostasis by conventional means is difficult to secure (for example during endoscopic surgery), for the obliteration of sinuses and fistulae; and for sealing perforations of hollow visci such as the stomach or duodenum (either used alone or in conjunction with a tissue or artificial patch In a still further embodiment of the invention, the use of tissue cement proteins is provided as tools in the study of cement cone assembly and in the development of strategies to prevent cement cone assembly, and thereby inhibit tick attachment and feeding. For example, monoclonal antibodies and engineered vaccines directed against tissue cement proteins could be used to prevent parasite feeding.

Arthropod parasites are sources of infectious disease agents such as tick-borne encephalitis virus, Crimean-Congo haemorrhagic fever virus, Nairobi sheep virus, *Borrelia burgdorferi* (the agent of lyme disease), *Theileria parva* (the agent of East Coast fever) and other injurious effects that have major impacts in human and veterinary medicine. Control of the arthropod parasites currently relies primarily on the use of chemicals such as acaricides.

Attempts have been made to use immunological means of control through vaccine technology. Some success has been met in identifying certain protective antigens of arthropod parasites as being potential vaccine candidates, but only a few have as yet come to commercial fruition, most notably for the cattle tick *Boophilus microplus*. Despite these developments, there is nonetheless a continuing need for arthropod parasite vaccines and in particular for a vaccine which may be used against ticks An alternative vaccine strategy that has until now not been possible is to vaccinate animals using purifed antigens The immune system of the animal thus develops an improved humoral response to these antigenic polypeptides and correspondingly develops resistance against the arthropod parasites themselves One disadvantage of using vaccines directed against a specific vector-transmitted disease to control that disease is that a different vaccine is usually required to protect against each disease. Vaccines directed against disease vectors (such as ticks and mosquitoes) have an added advantage in that their effect may control several different infections, as long as these infections are transmitted by only one type of disease vector.

The present invention therefore also provides for the use of tissue cement proteins as defined above as immunogens. Accordingly, a further aspect of the present invention comprises a vaccine comprising one or more tissue cement proteins as defined above in an arthropod parasite vaccine and in particular as protective immunogens in the control of diseases caused by infections transmitted by arthropod parasites.

The vaccine may be administered singly, or in combination with other immunogens. The vaccine may include adjuvants of the type which are well known in the art, for example, alum. Suitable candidates for vaccination include humans and domesticated animals such as cattle, goats, sheep, dogs, cats and other mammalia. All these species require protection against arthropod parasites, particularly ticks, and the infections they transmit.

According to a further aspect of the present invention there is provided a nucleic acid molecule encoding a tissue cement protein as defined above, or any functionally equivalent form. The nucleic acid sequences of choice comprise or contain the nucleic acid sequences exhibited in FIGS. 2 to 8 (SEQ ID NOS: 2, 4, 5, 7, 12, 13 or 15). The skilled man will appreciate that changes may be made at the nucleotide level by addition, substitution, deletion or insertion of one or more nucleotides, which changes may or may not be reflected at the amino acid level, dependent on the degeneracy of the genetic code.

The nucleic acid molecule according to this aspect of the present invention may comprise DNA, RNA or cDNA and may additionally comprise nucleotide analogues in its sequence. Preferably, the nucleic acid comprises DNA, more preferably single or double-stranded cDNA.

Antisense sequences may also be designed with respect to the nucleic acids of this aspect of the invention and in sequence will in whole or in part comprise that of the complementary strand to the coding nucleic acid strand. Oligonucleotides comprising antisense sequences to tissue cement protein genes may be used as diagnostic tools in the detection of organisms or vectors expressing nucleic acids that encode tissue cement proteins. These single-stranded oligonucleotides will comprise lengths of nucleic acid of between 10 and 300 nucleotides, preferably between 10 and 100 nucleotides, most preferably of between 10 and 30 nucleotides. The oligonucleotides may be labelled in order to aid their detection. Suitable labelling systems are well known in the art.

Methods for screening cDNA libraries for proteins analogous to the tissue cement proteins described herein will be apparent to the man of skill in the art The antisense sequences of this aspect of the invention therefore may not correspond exactly to the complementary strand of the nucleic acid that encodes a tissue cement protein. For example, when using antisense oligonucleotides as probes in the screening of a cDNA library for proteins analogous to the tissue cement proteins described herein, due to the degeneracy of the genetic code and inter-species sequence divergence, any analogous genes to those described herein are likely to comprise sequences that are significantly different to that of the probe.

Accordingly, antisense sequences for use in accordance with this aspect of the present invention comprise sequences that hybridise under standard conditions to the nucleic acid sequences exhibited in FIGS. 2 to 8 (SEQ ID NOS: 2, 4, 5, 7, 12, 13 or 15). Hybridising sequences' included within the scope of the invention are those binding under standard conditions. As used herein, by 'standard conditions' is meant both non-stringent standard hybridisation conditions (6×SSC/50% formamide at room temperature) with washing under conditions of low stringency (2×, room temperature, or 2×SSC, 42° C.) or at standard conditions of higher stringency, e.g. 2×SSC, 65° C. (where SSC=0.15M NaCl, 0.015M sodium citrate, pH 7.2). Preferably standard conditions refers to conditions of high stringency.

A further aspect of the present invention comprises a method of production of a tissue cement protein which method comprises expression from the encoding nucleic acid therefor Expression may conveniently be achieved by culturing under appropriate conditions recombinant host cells containing the nucleic acid.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

The expression of heterologous polypeptides and polypeptide fragments in prokaryotic cells such as *E. coli* is well established in the art; see for example *Molecular Cloning: a Laboratory Manual:* 2nd edition, Sambrook et al., 1989, Cold Spring Harbor Laboratory Press. Expression in eukaryotic cells in culture is also an option available to those skilled in the art for the production of heterologous proteins; see recent reviews, for example O'Reilly et al., (1994), Baculovirus expression vectors—a laboratory manual, Oxford University Press.

Suitable vectors can be chosen or constructed for expression of tissue cement proteins, containing the appropriate regulatory sequences, including promoter sequences, terminator sequences, polyadenylation sequences, enhancer sequences, marker genes and other sequences as appropriate. Vectors may be plasmids, viral e.g. bacteriophage, or phagemid, as appropriate. For further details see *Molecular Cloning: a Laboratory Manual* (loc. cit). Many known techniques and protocols for manipulation of nucleic acid, for example, in the preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. For example, in eukaryotic cells, the vectors of choice are virus-based, such as baculovirus-based A further aspect of the present invention provides a host cell containing a nucleic acid encoding a tissue cement protein or functional equivalent thereof A still further aspect provides a method comprising introducing such nucleic acid into a host cell or organism Introduction of nucleic acid may employ any available technique. In eukaryotic cells, suitable techniques may include calcium phosphate transfection, DEAE-Dextran-mediated transfection, electroporation, liposome-mediated transfection or transduction using retrovirus or other viruses, such as vaccinia or, for insect cells, baculovirus In bacterial cells, suitable techniques may include calcium chloride transformation, electroporation or transfection using bacteriophage.

Introduction of the nucleic acid may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

Transgenic animals transformed so as to express or overexpress in the germ line one or more tissue cement proteins or functional equivalents as described herein form a still further aspect of the invention, alone with methods for their production. Many techniques now exist to introduce transgenes into the embryo or germ line of an organism, such as those illustrated in Watson et al., (1994) Recombinant DNA (2nd edition), Scientific American Books.

Various aspects and embodiments of the present invention will now be described in more detail by way of example, with particular reference to tissue cement proteins isolated from ticks, and especially from *Rhipicephalus appendiculatus*. It will be appreciated that modification of detail may be made without departing from the scope of the invention

BRIEF DESCRIPTION OF THE FIGURES

FIG. 1A is an SDS-gel containing male and female salivary gland extract (SGE) and male and female cement polypeptides obtained by rinsing cement cones in PBS.

FIG. 1B is the corresponding Western blot to FIG. 1A, probed with a polyclonal antiserum raised against a 17 Kd protein purified from tick salivary gland extract.

FIG. 2 is a partial cDNA sequence (SEQ ID NO: 2) and translation product of (SEQ ID NO: 1) clone 21. The cDNA-inferred protein is a cement protein; it contains a hydrophobic N-terminal region which possibly constitutes a signal sequence, typical for secreted proteins. The protein strongly resembles other structural proteins, especially keratin. A recognition sequence for post-translational attachment of glycosaminoglycan groups is underlined.

FIG. 3 is the cDNA (SEQ ID NO: 5) and cDNA-inferred polypeptide sequence (SEQ ID NO: 11) of clone 33. A putative signal sequence is given in bold. Like many structural proteins, this protein is glycine- and proline-rich. The protein also displays some resemblance to keratins.

FIG. 4 is a partial sequence of cemA cDNA (SEQ ID NO: 12) and the cDNA-inferred polypeptide sequence (SEQ ID NOS: 3). The protein is very repetitive, with the sequence KGALLQQQQASQVKGALKAI, or slight variants thereof, repeated several times.

FIG. 5 is a partial cDNA (SEQ ID NO: 4) and cDNA-inferred polypeptide sequence (SEQ ID NOS: 6) of clone 24. The protein has resemblance to structural proteins (amongst others collagen), and is contains repeats. The cDNA also has a region in common with glutenin, a self-assembling protein.

FIG. 6 is a partial cDNA (SEQ ID NO: 13) and cDNA-inferred sequence (SEQ ID NO: 14) of clone 68. The encoded proteins resemble structural proteins, such as keratin A series of putative glycosaminoglycan attachment sites are underlined.

FIG. 7 is the complete cDNA sequence (SEQ ID NO: 15) and cDNA-inferred polypeptide sequence (SEQ ID NO: 16) of clone 64. The putative signal sequence is give in bold. A possible glycosaminoglycan attachment site is underlined. The first 40 amino-acid section of the mature protein is collagen-like, whilst the remainder of the sequence resembles keratin. The protein is glycine-rich and contains several repeats of the motif (C/S)1-4(Y/F), which is also found in structural proteins from insect egg shells. The tyrosines may be involved in cross-linking by formation of dityrosine-bridges by phenoloxidases. A similar protein is encoded by clone I (see FIG. 8).

FIG. 8 is a partial cDNA-sequence (SEQ ID NO: 7) and cDNA-inferred polypeptide sequence (SEQ ID NO: 17) of clone I. The inferred protein is glycine- and tyrosine-rich and resembles a cement protein of the reef-building polychaete *Pragmatopoma californica* (a component of the quinone-tanned cement in the tubes built by these marine worms).

FIG. 9 is a DNA alignment between the protein sequence shown in FIG. 8 (SEQ ID NO: 8) and a cement protein from the polychaete *Pragmatopoma californica (SEQ ID NO:* 9).

FIG. 11.*a* and 11.*b* show alignments of the truncated clone 64 protein with various natural proteins.

EXAMPLES

Ticks

Figure 10:
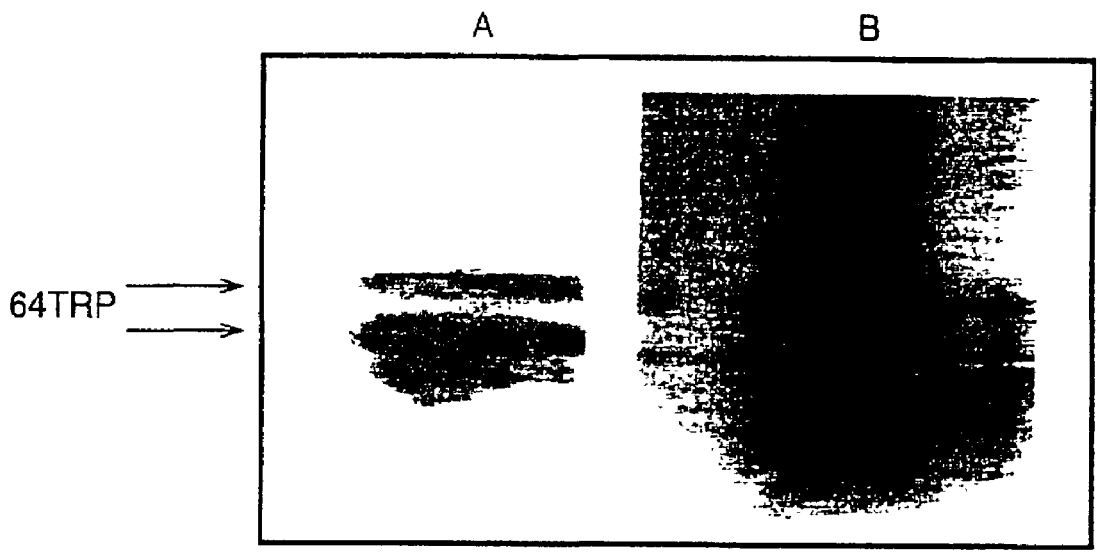
FIG. 10A shows a PAGE gel showing the proteins expressed from *E. coli* cells transformed with a truncated coding sequence from clone 64.
FIG. 10B shows a Western blot corresponding to FIG. 10A.

Ticks were reared according to Jones et al, (1988). All three developmental stages of *Rhipicephalus appendiculatus* were fed on Dunkin Hartley guinea pigs. When not feeding, all ticks were maintained at 21-26° C. and at 85% relative humidity.

Example 1

Identification of Proteins

Cement cones were collected from ticks (nymphs and adults) feeding on guinea pigs at different points of the attachment period. The cones were homogenised in phosphate-buffered saline (PBS), to extract soluble proteins, and in hot alkali and acid to extract less soluble components (Kemp et al., 1982, Jaworski et al., 1992).

Protein patterns were analysed using SDS-PAGE; the resulting gel is displayed as FIG. 1A. Bands or spots corresponding with early expressed (group A) proteins and later expressed (group B) proteins were excised from the gel and used for the production of polyclonal antiserum. Good antisera could be obtained even against the less antigenic proteins provided that these proteins were not allowed to renature completely.

The resulting antisera were used to screen cDNA libraries and also for immunoblotting (see FIG. 1B) and immunohistochemistry.

Proteins for which no good antiserum could be raised were blotted onto polyvinylidene difluoride membranes for amino-terminal sequence determination. For amino acid sequencing, samples were run on an Applied Biosystems 494A "Procise sequencer" (Perkin-Elmer, Applied Biosystems Division, Warrington U.K.). Electroblotted samples are run using Applied Biosystems "Mini-Blott" cartridge in the place of the standard cartridge. Bands of interest are excised from the membrane and cut into 1×3 mm pieces for insertion into the cartridge. These are sequenced using the manufacturer's recommended programme for membrane-bound samples (Schagger and von Jagow, 1987; Matsudaira, 1987)

This information was then used to design oligonucleotides to screen a tick cDNA library for clones of interest

Example 2 cDNA Library Construction

Salivary glands were excised from 20 male and 20 female adult *R appendiculatus* specimens that had been feeding on guinea pigs for two days. The glands were collected on dry ice in an Eppendorf tube. Messenger RNA was isolated using the FastTrack mRNA isolation kit (Invitrogen).

To synthesize cDNA and insert the cDNA into the Lambda Zap II vector, the ZAP cDNA synthesis kit (Stratagene) was used Prior to unidirectional insertion of the cDNA into the lambda vector, the nucleic acid was fractionated over a Sephacryl S-400 column (Phamacia).

A library (termed d2-I) was constructed from low molecular weight cDNAs (ranging from approximately 100 to 2,000 base pairs). The higher molecular weight fraction was used to construct a second library (d2-II). Packaging was performed using Packagene (Promega) packaging extracts. Approximately $1.5 \times 10^6$ plaque-forming units (PFU) of each library were amplified in XL-1-Blue cells (Stratagene) for subsequent use.

Example 3

Screening of the d2-II cDNA Library

Phagemids were excised in vivo from a randomly selected fraction of the library, and used to generate double-stranded pBluescript SK(–) plasmids in XL1-Blue cells (Stratagene), as described by Short et al, (1988)

XL1-Blue colonies were plated out on ampicillin-containing LB (Luria-Bertani) agar plates, supplemented with 5-bromo-4-chloro-3-indolyl-β-D-galactopyranoside (X-Gal. Melford Laboratories, UK) and isopropyl-β-D-thiogalactopyranoside (IPTG, Novabiochem) tor blue/white colony selection About 75 plasmids (from white colonies) with inserts ranging from 250 to 1000 base pairs (as determined by digestion with PvuII and electrophoresis over a 1% agarose gel) were selected for sequencing. The oligonucleotides used for sequencing correspond to the T3 and T7 primer sites in the pBluescript plasmid DNA.

Example 4

Sequencing

Plasmids were purified from overnight cultures according to Goode and Feinstein (1992), alkali-denatured (Mierendorf and Pfeffer, 1987), and sequenced using the Sanger dideoxy-mediated chain termination reaction (Sanger and Coulson, 1975). Sequence data were analysed using the GCG sequence analysis software (Program Manual for the Wisconsin Package, 1994).

Protein database searches were performed at the National Centre for Biotechnology Information (NCBI) using the BLAST network service.

A number of clones were sequenced or partially sequenced. The sequences or partial sequences of those clones are shown in FIGS. 2 to 8 (SEQ ID NOS: 2, 4, 5, 7, 12, 13 or 15) attached hereto. Explanations of the structure and features of the cloned sequences are given in the Brief description of the Figures above and in other parts of the description.

Example 5

Production of the CemA Antiserum

An antiserunm was produced against a prominent salivary gland protein of around 17 kDa size For production of the polyclonal antiserum, salivary glands taken at day 6 of the adult feeding stage were homogenised in phosphate-buffered saline (PBS) and submitted to centrifugation (3 min; 12,000×g). The proteins in the supernatant [i e. the salivary gland extract (SGE)] were resolved over a 15% SDS-polyacrylamide gel, according to Laemmli (1970).

The gel was stained in an ice-cold 100 mM KCl solution and the 17 kDa protein was excised. The polyacrylamide section containing the protein was dried under vacuum, homogenised in PBS, mixed with an equal volume of Montanide ISA 50 adjuvant (Seppic, France) and subcutaneously injected into Dunkin Hartley guinea pigs. This procedure was repeated every 10 days. Serum was collected 10 days after the 4th injection.

Western blotting, performed according to Kyhse-Anderson (1984), showed a strong reaction of the antiserum with a 17 kDa protein from the surface of cement cones (see FIG.

1A). This protein, termed CemA, was present at all feeding stages of the ticks and could be easily obtained by washing of the cement cones in PBS.

Example 6

Immunohistochemistry/western Blotting/northern Blotting/in situ Hybridisation

The polyclonal antisera were used in western blots and in staining sections of cement cones and salivary glands, taken at different stages of the feeding period. Where light-microscopy did not provide sufficient resolution to visualise the stain, electron microscopy was used.

For proteins against which no antisera could be produced, northern blots were instead performed using digoxygenin-labelled DNA probes constructed by random primer labelling (Sambrook et al., 1989) using purified insert from the original clones. An anti-digoxygenin antiserunm conjugated with alkaline-phosphatase allows probe detection In fact, in situ hybridisation may be more suitable for localising and following the expression of genes in the salivary glands, since immunohistochemistry when performed on salivary glands often results in a high background.

In conjunction with the SDS-PAGE data, these techniques allow determination of the times at which specific proteins were expressed during the feeding period, where in the salivary glands they were produced and to which layer of the cone they contribute (thus better defining group A and B proteins).

Example 7

Construction of Genomic Libraries and Examination of Differential Expression.

In order to evaluate the differential expression of tissue cement protein genes, the following procedure is presently being followed. Genomic tick DNA, digested with suitable endonucleases is inserted into tile Lambda Fix II vector (Stratagene), which allows for easy restriction mapping. Digoxygenin-labelled cDNA probes are used for library screening.

Regions flanking the coding sequences and introns are being sequenced and examined for the presence of sites that might play a role in the ordered expression of the proteins (for example ecdysteroid or heat-shock response elements). It was thought that comparison of genes of proteins expressed simultaneously might reveal common upstream or downstream sequences that are responsible for the regulation of gene expression. All group A protein genes, for example, may have identical recognition sites for regulatory factors.

Prospective regulatory regions are coupled to a reporter gene, for example luciferase, transfected into suitable cells (e.g. *Drosophila* cells), and submitted to functional assays. Gel retardation, DNA protection or band-shift assays are also being performed to confirm the existence of functional regulatory domains It is possible that a single promoter region controls the simultaneous expression of a whole series of genes These genes are then most probably localised im close proximity to one another on the genome. To investigate this possibility, the digoxygenin-labelled probes are being used to localise the genes on the genome by means of in situ hybridisation, Southern blotting and genomic library screening.

Expression of cement proteins may be regulated by one or more haemolymph-borne factor(s). This possibility is being investigated by incubating salivary glands taken from animals that have only just attached to their host in tissue culture medium containing haemolymph from ticks that have been feeding for 24 or 48 hours. Blotting (northern and western) or reverse transcriptase-PCR is then used to determine whether genes have been switched on or off.

Where there is evidence for a haemolymph-borne factor controlling the expression of cement genes, transplantation of salivary glands from ticks early in the feeding stage, to animals later in the feeding stage is being carried out, in case in vitro incubation experiments do not provide adequately clear results. This factor has been identified by HPLC and other standard techniques.

Example 8

Aggregation/cross-linking Studies—Protein Expression

Aggregation (polymerisation) and cross-linking are being determined using proteins extracted from salivary glands and cement cones, and also using expressed recombinant proteins. Cement cone proteins are being examined directly by protein hydrolysis followed by detection of di- or tri-tyrosines among the amino-acids. Other assays are also being used for the detection of cross-linking enzymes and SDS-PAGE in the presence and absence of reducing agents to reveal inter- or intramolecular disulphide-bridges.

In addition, native group A and group B proteins are isolated from cement and salivary gland extracts by means of immunoprecipitation. This is only possible for the more soluble proteins. The molecular weight of the precipitated proteins is being determined by gel filtration Comparisons are being made to the molecular weight of monomers as determined by SDS-PAGE and western blotting, or as calculated from the cDNA derived protein sequences.

Other components co-precipitating with a given (A or B) protein are being identified by screening the cDNA-library with oligonucleotide probes designed using N-terminal amino acid sequences The nature of eventual intermolecular bonds are also being determined. Hydrogen-bonds can be destroyed with urea and hydrophobic interactions with detergents. Detection of disulphide-bridges and cross-linked amino-acids can be performed as described previously (Creighton 1989; Malencik et al., 1996).

Studying native proteins is not always straightforward. For example, it can be difficult to extract enough protein to enable exhaustive study. Also, non-specific protein interactions may occur. Many of these problems can be solved by the use of recombinant proteins in their place.

Recombinant group A and group B proteins are therefore being expressed in bacteria or, where glycosylation and other post-translational modifications are crucial, in a eukaryotic (baculoviral) system. Those proteins which are not very soluble can be expressed in fusion with thioredoxin using, for example, the ThioFusion system (Invitrogen). In this system, the proteins are provided with oligohistidine-tags, allowing easy purification be means of nickel-agarose chromatography (Janknecht et al., 1991). Enterokinase and/or thrombin sites are incorporated to remove tags and fused proteins from the cement protein after purification, in cases where this is necessary. In case aggregation of a protein takes place, or if interaction occurs between, for example, two different group A proteins, the nature of the bonds must be determined, as for the native proteins—see above. Expressed proteins which can be recognised at all times by their histidine tags, or by the antisera were incubated with salivary gland extracts, in the absence and presence of specific and non-specific enzyme-inhibitors, in order to identify cross-linking.

The histidine-tagged expressed proteins can then be coupled to nickel-agarose and used in affinity-chromatography (Bugge et al., 1992, Lu et al., 1993) to isolate interacting proteins from salivary gland extracts or cement cones. These proteins can then be identified through the screening of cDNA libraries. By deletion and mutation experiments, domains or residues participating in the aggregation or cross-linking of recombinant proteins, are thus being identified.

Example 9

Expression of Truncated Cement Protein (64TRP) in Bacteria

Oligonucleotides with appropriate restriction enzyme sites were designed to permit PCR cloning of an N-terminal fragment of clone 64, as shown in FIG. 7 (SEQ ID NO: 16). This fragment, known as 64P (amino acids 34 to 85) from the cDNA, was PCR cloned in-frame into the pET23 vector (Novagen). The construct, 64TRP (encoding amino acids 34 to 85), tagged onto the 6×His-Tag of the pET23 vector, was obtained using standard PCR cloning methods (Sambrook et al., 1989). The plasmid was transformed into E. coli AD494 cells (Sambrook et al., 1989).

The expressed histidine-tagged expressed 64TRP (truncated cement protein) was purified by means of nickel-agarose affinity chromatography (Janknecht et al., 1991). The protein was analysed by SDS-PAGE (Leammli, 1970) and the resulting gel is shown in FIG. 10A. The expected protein band of approximately 7.8 kDa in size was obtained plus an extra upper band of about 10 kDa. The apparent size of the upper band indicates that it is not a dimer. Amino-terminal sequence analysis (Schagger and von Jagow, 1987; Matsudaira, 1987) of the two bands is currently being performed to determine the relationship between the two bands. A corresponding Western blot is shown in FIG. 10B.

Example 10

Expression of Full-length Cement Protein (64P) in Insect Cells Using Recombinant Baculovirus The full length clone of the cement protein 64P (i.e. 144 amino acids in length) was amplified from the cDNA using oligonucleotides containing appropiate restriction enzyme sites, inserted into the C129 kHis baculovirus vector and transfected into Sodoptera figiperda insect cells for eukaryotic expression (O'Reilly et al., 1994).

Example 11

Similarity of the Amino Acid Sequence of the R. appendiculatus Cement Protein to Sequences of Other Structural Proteins Protein database searches were performed at the National Centre for Biotechnology Information (NCBI) using the BLAST for the amino acid sequences of both the truncated and full length clone of the cement protein. FIGS. 11a and 11b show the relationships between the 64P, the truncated 64TRP and other structural proteins.

The first 40 amino acids of the cement protein are strongly collagen-like (FIG. 11b) and the rest of the sequence resembles keratin (FIG. 11a). The protein is glycine-rich and contains several repeats of the motif (C/S) 1-4(Y/F) resembling structural proteins from Drosophila melanogaster (cuticular protein) and other insect egg shells, as well as vertebrate cytokeratins including mammalian keratin complex 2 basic protein, mouse keratin, human keratin, collagen type IV alpha and IPIB2 precursor. It would seem that the cement protein has been designed to resemble the skin proteins of the host, with the most likely aim of avoiding rejection of skin-tick attachment by the host's natural immune defence mechanisms. The compositional resemblance of 64P with its surrounding tissues may also facilitate the intimate binding between the cement cone and the surrounding skin tissues (see Examples 12 and 13).

Example 12

Histological Studies

Figure 12A:
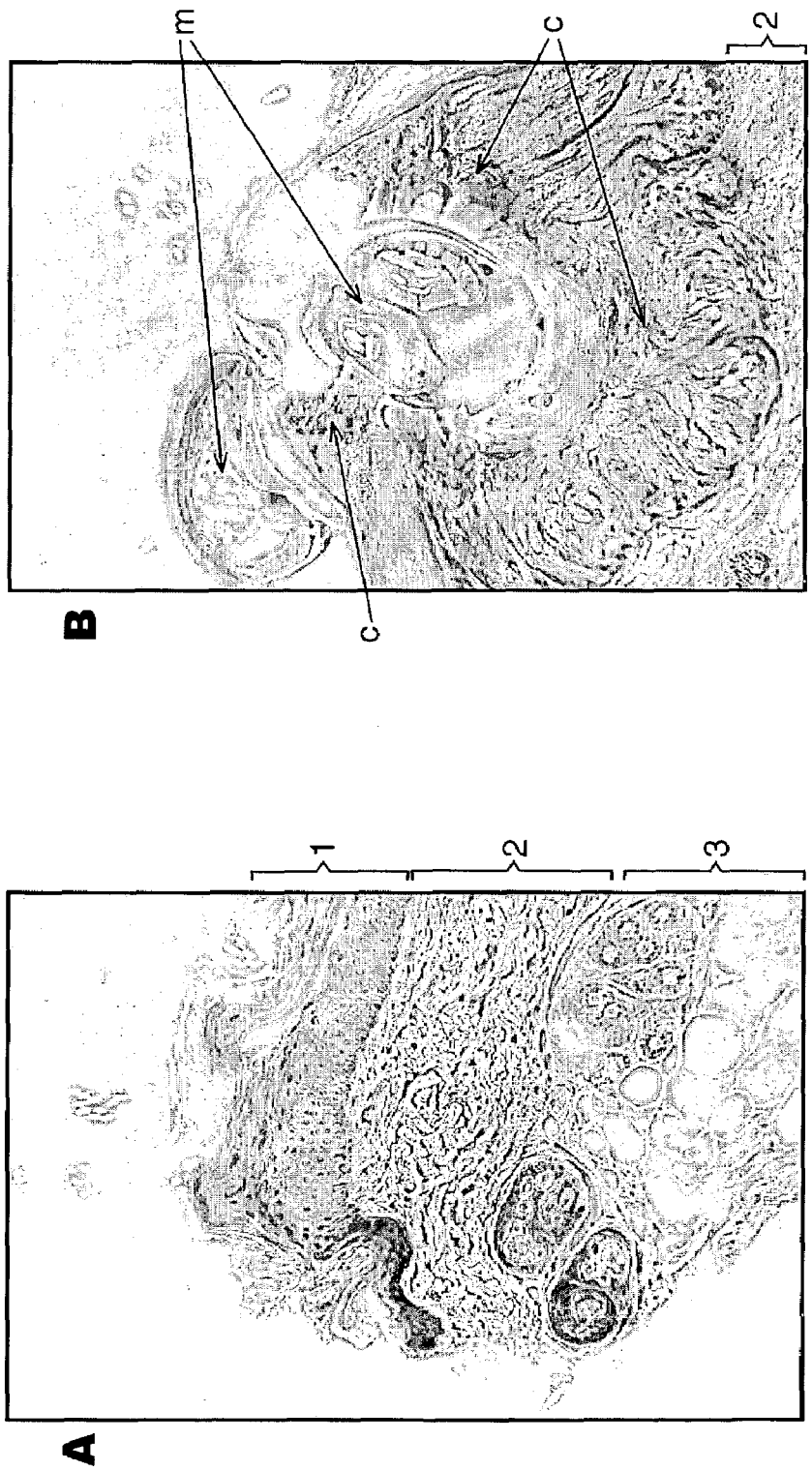
FIGS. 12.*a* and 12.*b* show histological sections of hamster skin stained with various conventional stains.

Histological studies using either haematoxylin and cosin or van Gieson stains (Bancroft and Stevens, 1990) were performed on normal hamster skin sections and on hamster skin sections on which R. appendiculatus ticks had been fed. FIG. 12.a.A shows a normal skin section with intact epidermal, dermal and subcutaneous layers. The haematoxylin and cosin, and van Gieson stains indicate the expected tissue-types (i.e. basement membranes, collagen fibers and reticular fibers.) In skin sections on which R. appenidiculatus had fed, the tick cement cone is clearly attached to the skin (FIG. 12.b.A) and can be seen embedded in the dermis (FIGS. 12.a.B and 12.b.B) with the mouth parts in situ. Comparatively, the cement cone seems to resemble normal skin basement membranes, collagen/reticulin fibers, in tissue stain uptake. Also, there is no evidence of infiltration by inflammatory cells in relationship to the cement cone. The apparent absence of inflammation adds credence to the hypothesis that the structure and composition of the cement cone resembles that of skin tissues and is designed to avoid provoking a host response against the tick. The layered structure of the cement cone is clearly distinguishable in FIG. 12.a.B. The apparent layering is probably due to the discontinuous deposition of cement proteins as the tick alternates between salivation (i.e. secretion) and imbibing of host fluids.

Example 13

Immunohistochemical Studies/Western Blotting

The denatured recombinant 64TPP protein was further purified by cation-ion exchange chromatography according to the manufacturer's recommendations (Pharmacia). The purified protein was used to raise polyclonal antiserum by subcutaneous injections of equal volumes of protein and Montanide ISA 50 adjuvant into Dunkin Hartley guinea pigs.

Western blotting (Kyhse-Anderson (1984)) showed a strong reaction of the antiserum to the denatured recombinant 64TRP cement protein bands (FIG. 11B). Western blots with R. appendiculatus salivary gland and cement cone extracts from male and female ticks (prepared as previously described in Example 5) showed no reaction with the antiserum. The most probable explanation for the negative results is that the anti-64TRP antiserum binding epitope(s) were not readily available on the extracted proteins owing to the conformation of the proteins Using the anti-64TRP antiserum, immunohistochemical studies were performed on sections of both normal hamster skin, and *R. appendiculatus* salivary glands, cement cones and cement cones attached to hamster skin on which *R. appendiculatus* ticks had been attached (Coligan et al., 1991).

Figure 13A:
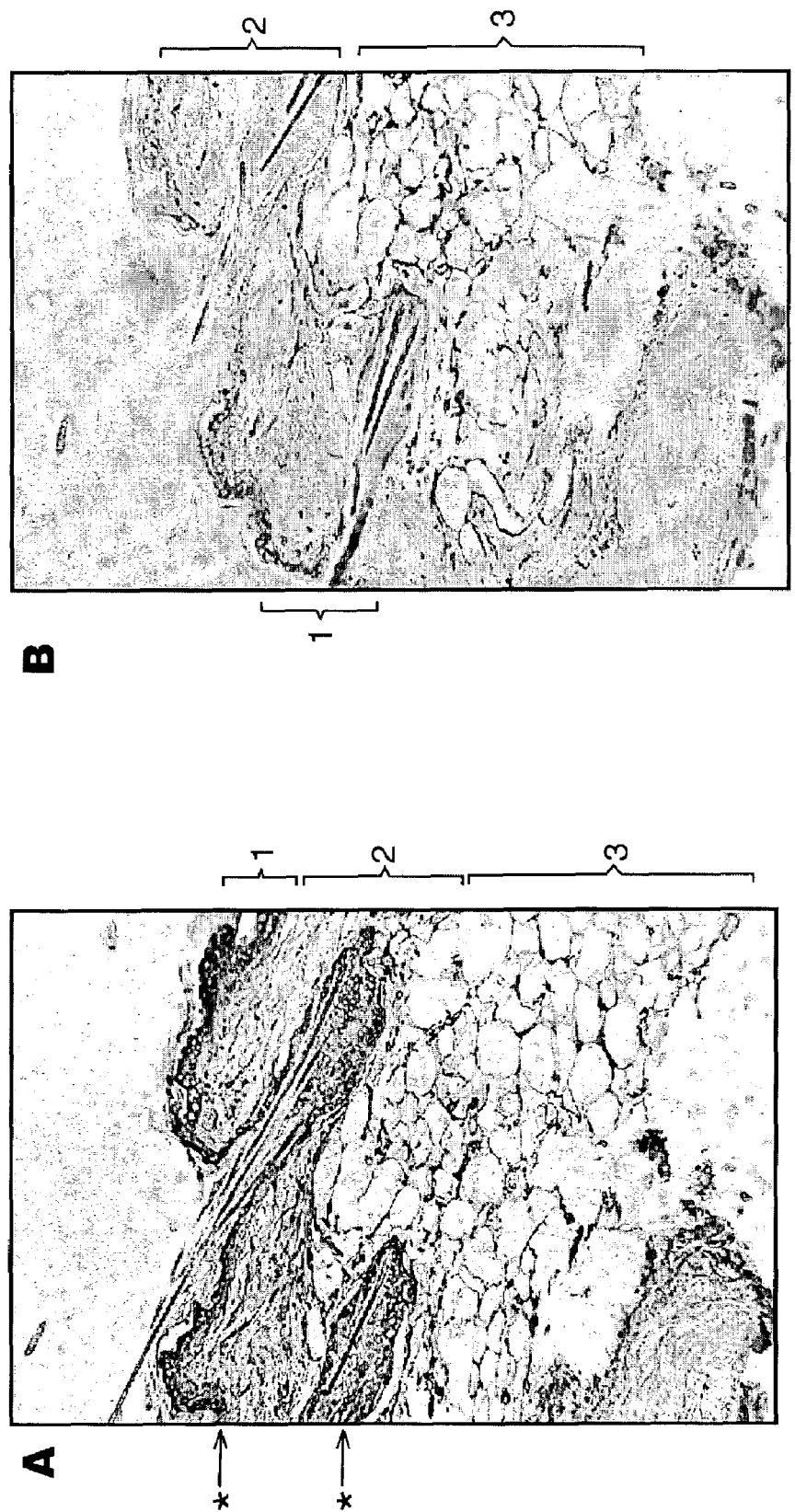
FIGS. 13.*a*, 13.*b* and 13.*c* show immunoperoxidase-stained sections of hamster skin.
Figure 13C:
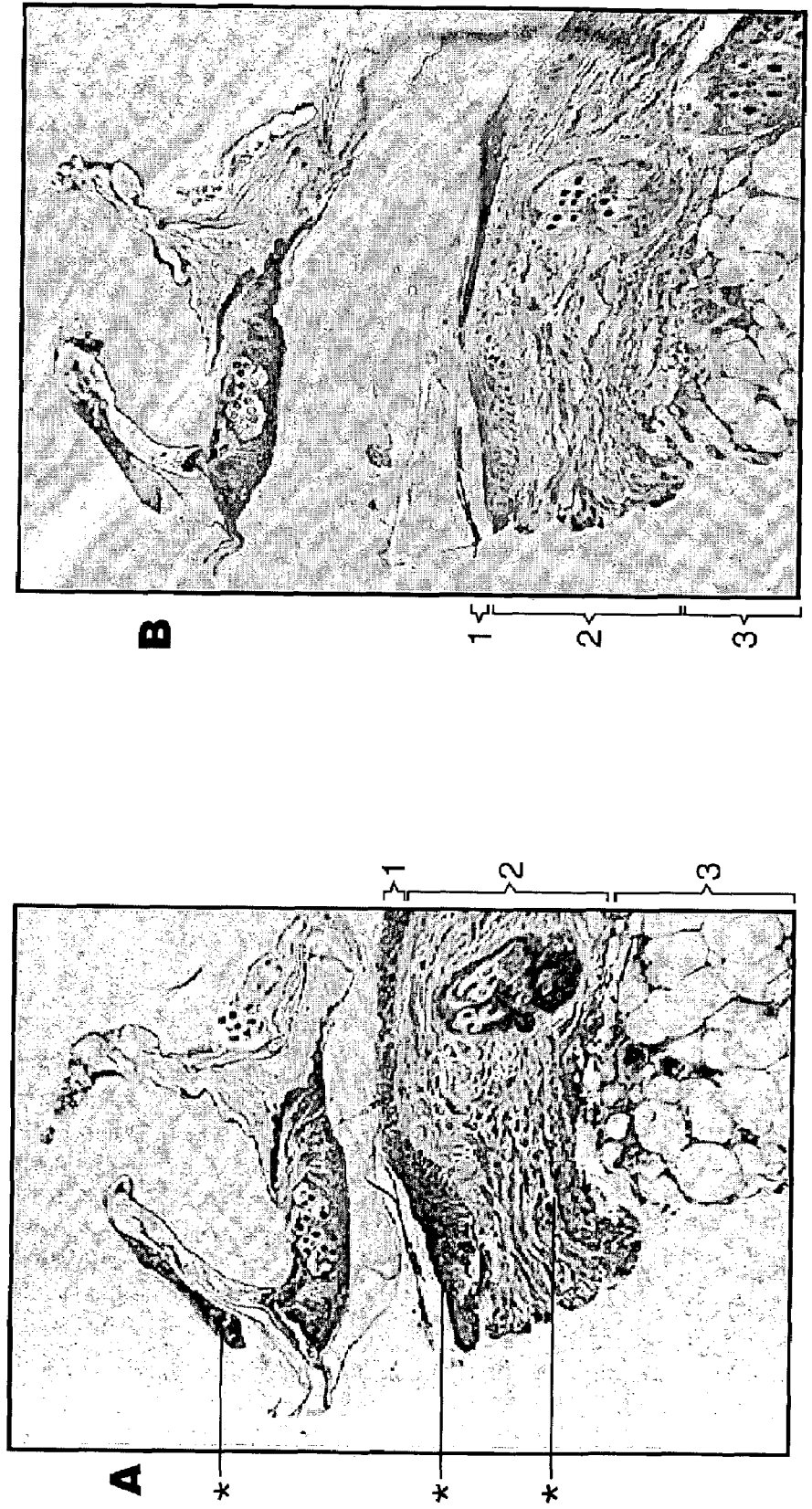

Using normal skin, the anti-64TRP antiserum reacted strongly with the basement membranes, epidermal and dermal tissues as well as the hair follicular structures (compare FIG. 13.*a*.A with the control serum, FIG. 13.*a*.B). In skin from hamsters on which ticks had been fed, sections of individual cement cones reacted with the antiserum (FIG. 13.*b*. and FIG. 13.*c*.). The reactions were mainly with the outermost layer and inner layer attached to the basement membrane of the skin. The reaction pattern with cement cones may indicate that 64P is a cement protein that lines the cement cone, possibly acting as a glue that binds the cement cone to the surrounding epidermal and dermal tissues.

REFERENCES

Arthur D. R. (1951) *Parasitology* 41, 66-81.
Brown S J. and Askenase P W (1986) *Exp. Parasitol.* 62, 40-50
Bugge T. H., Pohl J., Lonnoy O. and Stunnenberg H. G. (1992) *Embo J.* 11, 1409-1418.
Creighton T., (1989) *Protein Structure—A practical approach*, IRL Press. 155-168.
Davies F. (1988) In: Monath, T. P. (Ed.) *The Arboviruses: Epidemiology and Ecology*, CRC Press. Inc., Boca Raton, Fla., 191-203.
Goode B. L. and Feinstein S. C. (1992) *Biotechniques* 12(3), 374-375.
Ichinose A., Bottenus R. E. and Davie E. W. (1990) *J. Biol. Chem.* 265, 13411-13414.
Janknecht R., de Martynoff G., Lou J., Hipskind R. A., Nordheim A., and Stunnenberg H. G. (1991) *PNAS* 88, 8972-8976.
Jaworski, D. C., Rosell R., Coons, L. B., and Needham G. R. (1992) *J. Med. Entomol* 29, 305-309.
Kemp D. H., Stone B. F. and Binnington K. C. (1982) In: Obenchain F. D. and Galun R. (Eds.) *Physiology of Ticks*. Pergamon Press, Oxford, New York, Toronto, Sydney, Paris, Frankfurt, 119-68.
Kyhse-Anderson J. (1984) *J. Biochem. Biophys. Methods* 10, 203-209.
Laemmli V. K. (1970) *Nature* 277, 680-685.
Lu T., Van Dyke M. and Sawadogo M. (1993) *Anal. Biochem.* 213, 318-322.
Malencik D. A., Sprouse J F., Swanson C. A. and Anderson S. R. (1996) *Anal Biochem* 242, 202-213
Matsudaira P. (1987) *J Biol. Chem.* 262. 10035-10038.
Mierendorf R. C. and Pfeffer D. (1987) *Methods Enzymol.* 152, 556-562.
Moorhouse D. E. and Tatchell R. J. (1966) *Parasitology* 56, 623-632.
Norval R. A. I., Barrett J. C, Perry B. D. and Mukhebi, A. W. (1992) In: Fizas B., Petney T. and Horak I. (Eds.) *Tick Vector Biology—Medical and Veterinary Aspects*. Springer-Verlag, Berlin Heidelberg.
Norval R. A. I., Perry B. D. and Young A. S. (1992) *The epidemiology of theileriosis in Africa*. Academic Press, London.
O'Reilly D. R., Miller L. K. and Luckow, V. A. (1994) *Baculovirus expression vectors—A laboratory manual*, Oxford University Press.
Sambrook et al., *Molecular Cloning: a Laboratory Manual*: 2nd edition, , 1989, Cold Spring Harbor Laboratory Press.
Sanger F. and Coulson A. R. (1975) *J. Mol. Biol.* 94(3), 441-448.
Schagger H. and von Jagow G. (1987) *Anal. Biochem.*, 166, 368-379.
Shapiro S. Z., Voigt W. P., and Ellis J. A. (1989) *Exp. Appl. Acarol.* 7, 33-41.
Siegel R. C. (1979) *Int. Rev. Conn. Tissue Res.* 8, 73-118.
Sonenshine D. E. (1991) *Biology of Ticks*, Vol. 1. New York Oxford, Oxford Univ. Press., 447.
Sugumaran M., Giglio L, Kundzicz H., Saul S. and Semensi V. (1992) *Arch. Insect. Biochem Physiol* 19.271-283.
Walker A. R., Fletcher J D. and Gill H. S (1985) *Int. J Parasitol.* 15, 81-100
Watson J. D., Gilman M., Witkowski J and Zoller M. (1994) *Recombinant DNA (2nd edition)*, Scientific American Books.

What is claimed is:

1. An isolated and purified tissue cement protein consisting of the amino acid sequence of SEQ ID NO: 16.

2. An isolated and purified tissue cement protein of claim 1 consisting of amino acids 34-85 of SEQ ID NO: 16.

3. The isolated and purified tissue cement protein of claim 1 that binds to vertebrate tissues.

4. The tissue cement protein of claim 1 isolated from ticks.

5. The tissue cement protein of claim 4 isolated from Ixodid ticks.

6. The tissue cement protein of claim 5 isolated from *Rhipicephalus appendiculatus*.

7. The isolated and purified tissue cement protein of claim 1, wherein said isolated and purified tissue cement protein further comprises one or more carbohydrate moieties.

8. The isolated and purified tissue cement protein of claim 7, wherein said carbohydrate moieties are glycosaminoglycan moieties.

9. A recombinant tissue cement protein consisting of the sequence of SEQ ID NO:16.

10. A fusion protein comprising the tissue cement protein of claim 1, wherein said tissue cement protein is genetically or chemically fused to one or more peptides or polypeptides.

11. A fusion protein comprising the tissue cement protein of claim 1, wherein said tissue cement protein is cross-linked to one or more peptides or polypeptides.

12. A fusion protein comprising the tissue cement protein of claim 1, wherein said tissue cement protein is attached to a label.

13. An immobilized tissue cement protein, wherein the tissue cement protein of claim 1 is bound to a support.

14. A vaccine comprising the isolated and purified tissue cement protein of claim 1 and a pharmaceutically acceptable excipient, wherein said vaccine inhibits tick feeding.

* * * * *